US008575101B2

(12) United States Patent
Schense et al.

(10) Patent No.: US 8,575,101 B2
(45) Date of Patent: Nov. 5, 2013

(54) SUPPLEMENTED MATRICES FOR THE REPAIR OF BONE FRACTURES

(75) Inventors: Jason Schense, Zurich (CH); John Watson, Zumikon (CH); Isabelle Arrighi, Zurich (CH)

(73) Assignee: Kuros Biosurgery AG, Zurich (CH)

( * ) Notice: Subject to any disclaimer, the term of this patent is extended or adjusted under 35 U.S.C. 154(b) by 45 days.

(21) Appl. No.: 13/167,488

(22) Filed: Jun. 23, 2011

(65) Prior Publication Data

US 2011/0311643 A1 Dec. 22, 2011

Related U.S. Application Data

(63) Continuation-in-part of application No. 11/327,214, filed on Jan. 6, 2006, now abandoned.

(60) Provisional application No. 60/641,715, filed on Jan. 6, 2005, provisional application No. 60/642,644, filed on Jan. 10, 2005.

(51) Int. Cl.
*A61K 38/29* (2006.01)
*A61K 9/00* (2006.01)
*C07K 14/635* (2006.01)

(52) U.S. Cl.
USPC ........ 514/11.8; 514/13.6; 514/16.7; 424/484; 530/382

(58) Field of Classification Search
None
See application file for complete search history.

(56) References Cited

U.S. PATENT DOCUMENTS

| | | | |
|---|---|---|---|
| 4,086,196 A | 4/1978 | Tregear | |
| 4,613,665 A | 9/1986 | Larm | |
| 4,810,784 A | 3/1989 | Larm | |
| 4,917,702 A | 4/1990 | Scheicher | |
| 5,069,905 A | 12/1991 | Lidor | |
| 5,100,668 A | 3/1992 | Edelman | |
| 5,171,670 A | 12/1992 | Kronenberg | |
| 5,202,247 A | 4/1993 | Kilburn | |
| 5,428,014 A | 6/1995 | Labroo | |
| 5,504,001 A | 4/1996 | Foster | |
| 5,510,370 A | 4/1996 | Hock | |
| 5,529,986 A | 6/1996 | Larsson | |
| 5,561,982 A | 10/1996 | Tunkel | |
| 5,582,862 A | 12/1996 | Reed | |
| 5,641,670 A | 6/1997 | Treco | |
| 5,693,341 A | 12/1997 | Schroeder | |
| 5,747,456 A | 5/1998 | Chorev | |
| 5,773,577 A | 6/1998 | Cappello | |
| 5,814,603 A | 9/1998 | Oldenburg | |
| 5,840,837 A | 11/1998 | Krstenansky | |
| 5,874,308 A | 2/1999 | Kilburn | |
| 5,874,500 A | 2/1999 | Rhee | |
| 5,877,153 A | 3/1999 | Harris | |
| 5,958,874 A | 9/1999 | Clark | |
| 6,054,122 A | 4/2000 | MacPhee | |
| 6,117,425 A | 9/2000 | MacPhee | |
| 6,136,564 A | 10/2000 | Kopetzki | |
| 6,197,325 B1 | 3/2001 | MacPhee | |
| 6,206,957 B1 | 3/2001 | Driessens | |
| 6,221,854 B1 | 4/2001 | Radomsky | |
| 6,303,138 B1 | 10/2001 | Peterson | |
| 6,331,422 B1 | 12/2001 | Hubbell | |
| 6,372,257 B1 | 4/2002 | Marchosky | |
| 6,468,543 B1 | 10/2002 | Gilbertson | |
| 6,468,731 B1 | 10/2002 | Hubbell | |
| 6,541,022 B1 | 4/2003 | Murphy | |
| 6,559,119 B1 | 5/2003 | Burgess | |
| 6,607,740 B1 | 8/2003 | Hubbell | |
| 6,608,293 B2 | 8/2003 | Kuderer | |
| 6,663,870 B2 | 12/2003 | Hart | |
| 6,730,721 B2 | 5/2004 | Bezemer | |
| 6,894,022 B1 | 5/2005 | Hubbell | |
| 6,960,452 B2 | 11/2005 | Hubbell | |
| 7,026,292 B1 | 4/2006 | Lee | |
| 7,045,105 B2 | 5/2006 | Lagow | |
| 7,052,856 B2 | 5/2006 | Ting | |
| 7,229,826 B2 | 6/2007 | Kale | |
| 7,241,730 B2 | 7/2007 | Hubbell | |
| 7,247,609 B2 | 7/2007 | Lutolf | |

(Continued)

FOREIGN PATENT DOCUMENTS

| | | |
|---|---|---|
| DE | 20010297 | 8/2000 |
| EP | 725145 | 8/1996 |

(Continued)

OTHER PUBLICATIONS

Adams, et al., "Roles of ephrinB ligands and EphB receptors in cardiovascular development: demarcation of arterial/venous domains, vascular morphogenesis, and sprouting angiogenesis," Genes & Development 13:295-306 (1999).

Baumgartner, at al., "Constitutive expression of phVEGF165 after intramuscular gene transfer promotes collateral vessel development in patients with critical limb ischemia," Circulation, 97:1114-1123 (1998).

Besson, at al., "Synthetic peptide substrates for a conductimetric assay of *Pseudomonas aeruginosa* elastase". Analytical Biochemistry, 237(2):216-223 (1996).

Blaess, et al., "Structural analysis of the sixth Immunoglobulin-like domain of mouse neural cell adhesion molecule LI and its interactions with av3, allb3 and a51 integrins," J Neurochem, 71:2615-2625 (1998).

(Continued)

*Primary Examiner* — Christina Bradley
(74) *Attorney, Agent, or Firm* — Pabst Patent Group LLP

(57) ABSTRACT

Supplemented matrices comprising a PTH releasably incorporated therein, optionally containing a granular material, which are used to heal bone fractures, particularly bone fractures with a risk of becoming delayed unions or non-unions, are described herein. The PTH is incorporated either through covalent linkage to the matrix or through non-covalent interaction with the matrix and/or the granules. These supplemented matrices decrease the time of healing compared to autograft and or trigger healing of bone fractures which otherwise would not heal. The matrices are biocompatible, preferably biodegradable, and can be formed in vitro or in vivo, at the time of implantation. The PTH may be a part of a fusion peptide. PTH can be incorporated into the matrices with full retention of its bioactivity. PTH can be releasably incorporated in the matrix.

18 Claims, 2 Drawing Sheets

(56) References Cited

U.S. PATENT DOCUMENTS

| | | | |
|---|---|---|---|
| 7,601,685 | B2 | 10/2009 | Hubbell |
| 2002/0168718 | A1 | 11/2002 | Hubbell |
| 2003/0012818 | A1 | 1/2003 | Schense |
| 2003/0103957 | A1 | 6/2003 | McKerracher |
| 2003/0166833 | A1 | 9/2003 | Lutolf |
| 2003/0180376 | A1 | 9/2003 | Dalal |
| 2004/0002770 | A1 | 1/2004 | King |
| 2004/0082513 | A1 | 4/2004 | Hubbell |
| 2005/0010297 | A1 | 1/2005 | Watson |
| 2005/0065281 | A1 | 3/2005 | Lutolf |
| 2005/0163817 | A1 | 7/2005 | Masters |
| 2005/0175665 | A1 | 8/2005 | Hunter |
| 2006/0147443 | A1 | 7/2006 | Schense |
| 2006/0148704 | A1 | 7/2006 | Schense |
| 2006/0168718 | A1 | 8/2006 | Watson |
| 2007/0010440 | A1 | 1/2007 | Schense |
| 2007/0179093 | A1 | 8/2007 | Lutolf |
| 2007/0202178 | A1 | 8/2007 | Schense |
| 2007/0254011 | A1 | 11/2007 | Schnabelrauch |
| 2007/0264227 | A1 | 11/2007 | Lutolf |

FOREIGN PATENT DOCUMENTS

| | | |
|---|---|---|
| WO | 8900051 | 1/1989 |
| WO | 9005177 | 5/1990 |
| WO | 9202620 | 2/1992 |
| WO | 9209301 | 6/1992 |
| WO | 9222312 | 12/1992 |
| WO | 9420133 | 9/1994 |
| WO | 9505396 | 2/1995 |
| WO | 9523611 | 9/1995 |
| WO | 9617633 | 6/1996 |
| WO | 9931137 | 6/1999 |
| WO | 950665 | 10/1999 |
| WO | 0010596 | 3/2000 |
| WO | 0044808 | 8/2000 |
| WO | 0064481 | 11/2000 |
| WO | 02085422 | 10/2002 |
| WO | 03040235 | 5/2003 |
| WO | 03052091 | 6/2003 |

OTHER PUBLICATIONS

Bonadio, at al., "Localized, direct plasmid gene delivery in vivo: prolonged therapy results in reproducible tissue regeneration" Nat Med., 5(7):753-9 (1999).
Borrajo, at al., "Derivatized Cyclodextrins as peptidometics: Influence on Neurite Growth," Bioorganic and Medicinal Chemistry Letters, 7:1185-90 (1997).
Brooks, et al., "Requirement of vascular integrin av3 for angiogenesis," Science, 264:569-571 (1994).
Bruckner, "EphrinB ligands recruit GRIP family PDZ adaptor proteins into raft membrane microdomains," Neuron, 22:511-524 (1999).
Calderwood, et al., "Integrins and actin filaments: reciprocal regulation of cell adhesion and signaling," J Biol Chem, 275:22607-22610 (2000).
Camarata, et al., "Sustained Release of Nerve Growth Factor from Biodegradable Polymer Microspheres," Neurosurgery Online, 30(3)313-319 (1992).
Cardin, et al., "Molecular Modeling of Protein-Glycosaminoglycan Interactions," Arterioscler Thromb. Vasc Biol, 9:21-32 (1989).
Conover, at al., "Disruption of Eph/ephrin signaling affects migration and proliferation in the adult subventricular zone," Nature Neuroscience, 3 (11):1091-3324 (2000).
Coombs, at al., "Directing sequence-specific proteolysis to new targets. The influence of loop size and target sequence on selective proteolysis by tissue-type plasminogen activator and urokinase-type plasminogen activator", J. Biol. Chem., 273(8):4323-4328 (1998).
Coussons, at al. "Factors that govern the specificity of transglutaminase-catalysed modification of proteins and peptides" Biochemical L., 282:929-30 (1992).

Dalva, et al., "EphB receptors interact with NMDA receptors and regulate excitatory synapse formulation," Cell, 103:945-956 (2000).
Deblois, et al., "Heparin-fibroblast growth factor-fibrin complex: in vitro and in vivo applications to collagen-based materials", Biomaterials., 15(9):665-72 (1994).
Dedhar and Hannigan, "Integrin cytoplasmic interactions and bidirectional transmembrane signaling," Current Opinion in Cell Biology, 8:657-669 (1996).
Dempster, et al., "Anabolic actions of parathyroid hormone on bone", Endocrine Rev., 14:690-709 (1993).
Dimilla, et al., "Mathematical model for the effects of adhesion and mechanics on cell migration speed," Biophys. J., 60(1):15-37 (1991).
Dinbergs, et al., "Cellular response to transforming growth factor-betal and basic fibroblast growth factor depends on release kinetics and extracellular matrix interactions," J. Biol. Chem., 271(47):29822-9 (1996).
Downs, et al., "Calcium Alginate Beads as a Slow-Release System for Delivering Angiogenic Molecules in Vivo and in Vitro," Journal of Cellular Physiology, 152:422-429 (1992).
Edelman, et al., "Basic fibroblast growth factor enhances the coupling of intimal hyperplasia and proliferation of vasa vasorum in injured rat arteries," J. Clin. Invest., 89 (2):465-73 (1992).
Edelman, et al., "Controlled and modulated release of basic fibroblast growth factor," Biomaterials., 12(7):619-26 (1991).
Edelman, at al., "Perivascular and intravenous administration of basic fibroblast growth factor: vascular and solid organ deposition," Proc. Natl. Acad. Sci. U.S.A., 90(4)1513-7 (1993).
Edgar, et al., "The heparin-binding domain of laminin is responsible for its effects on neurite outgrowth and neuronal survival," EMBO J., 3(7):1463-8 (1984).
Eliceiri and Cheresh, "The role of av integrins during angiogenesis: insights into potential mechanisms of action and clinical development," Journal of Clinical Investigation, 103:1227-1230 (1999).
Esposito and Caputo, "Mammalian transglutaminases. Identification of substrates as a key to physiological function and physiopathological relevance", FEBS J., 272(3):615-31 (2005).
Fasol, et al., "Experimental use of a modified fibrin glue to induce site-directed angiogenesis from the aorta to the heart," Journal of Thoracic and Cardiovascular Surgery, 107:1432-9 (1994).
Felding-Habermann, et al., "A single immunoglobulin-like domain of the human neural cell adhesion molecule L1 supports adhesion by multiple and platelet integrins," J Cell Biol, 139:1567-1581 (1997).
Feng, et al., "Roles for ephrins in positionally selective synaptogenesis between motor neurons and muscle fibers," Neuron, 25:295-306 (2000).
Ferrara, "Molecular and biological properties of vascular endothelial growth factor," J Mol Med, 77:527-543 (1999).
Ferrara and Alitalo, "Clinical applications of angiogenic growth factors and their inhibitors," Nature Medicine, 5:1359-1364 (1999).
Folkman, "Angiogenesis in cancer, vascular, rheumatoid and other disease," Nature Medicine, 1:27-31 (1995).
Gale, et al "Ephrin-B2 selectivity marks arterial vessels and neovascularization sites in the adult, with expression in both endothelial and smooth-muscle cells," Developmental Biology, 230:151-160 (2001).
Giannelli, et al., "Transforming growth factor-beta 1 triggers hepatocellular carcinoma invasiveness via alpha3beta1 integrin", Am J Pathol., 161(1):183-93 (2002).
Gotz, at al., "Neurotrophin-6 is a new member of the nerve growth factor family," Nature, 372(6503):266-9 (1994).
Grainger, et al., "Poly(dimethylsiloxane)-poly(ethylene oxide)-heparin block copolymers. I. Synthesis and Characterization," J. Biomed. Mater Res, 22 (3):231-249 (1988).
Griesler, et al., "Enhanced endothelial of expanded polyethrafluoroethylene grafts by fibroblast growth factor type 1 pretreatment," Surgery, 112:244-255 (1992).
Groenen, et al., "The carboxy-terminal lysine of alpha B-crystallin is an amine-donor substrate for tissue transglutaminase", Eur J Biochem., 205(2):671-4 (1992).
Grootjans, et al., "Substrate requirements for transglutaminases. Influence of the amino acid residue preceding the amine donor lysine in a native protein", J Biol Chem., 270 (39):22855-8 (1995).

(56) References Cited

OTHER PUBLICATIONS

Hall, "Molecular properties of fibrin-based matrices for promotion of angiogenesis in vitro," Microvascular Research, 62:315-326 (2001).
Hall, at al., "Trimerization of cell adhesion molecule L1 mimics clustered L1 expression on the cell surface: Influence on L1-Ligand Interactions and on promotion of neurite outgrowth," J of Neurochemistry, 75:336-346 (2000).
Hammoud, et al "Management of coronary artery disease: Therapeutic options in patients with diabetes," J Am. Col. Cardiology, 36:355-65 (2000).
Harada, et al., "Basic fibroblast growth factor improves myocardial function in chronically ischemic porcine hearts," J. Clin. Invest., 94(2):623-30 (1994).
Hata, et al., "Binding of lipoprotein lipase to heparin. Identification of five critical residues in two distinct segments of the amino-terminal domain," J. Biol. Chem., 268(12):8447-57 (1993).
Haugen, at al., "Central and peripheral neurite outgrowth differs in preference for heparin-binding versus integrin-binding sequences," J. Neurosci., 12(6):2034-42 (1992).
Herbert, et al., "Effects of fibinolysis on neurite growth from dorsal root ganglia cultured in two- and three-dimensional fibrin gels," J. Comp. Neural., 365 (3):380-91 (1996).
Herbert, et al., "Effects of fibrin micromorphology on neurite growth from dorsal root ganglia cultured in three-dimensional fibrin gels," J. Biomed. Mat. Res., 40 (4):551-9 (1998).
Hern, et al., "Incorporation of adhesion peptides into nonadhesive hydrogels useful for Tissue Resurfacing" J. Biomed. Mater. Res.. 39:266-276 (1998).
Houle & Johnson, "Nerve growth factor (NGF)—treated nitrocellulose enhances and directs the regeneration of adult rat dorsal root axons through intraspinal neural tissue transplants," Neuroscience Letters, 103:17-23 (1989).
Hubbell, "Bioactive biomaterials" Curr. Opinion Biotechnol., 10(2):123-129 (1999).
Humphries, "Integrin activation: the link between ligand binding and signal transduction," Curr Opin Cell Biol, 8:632-640 (1996).
Ilan, et al., "Distinct signal transduction pathways are utilized during the tube formation and survival phases of in vitro angiogenesis," J of Cell Science, 111:3621-3631 (1998).
Ingber and Folkman, "How does extracellular matrix control capillary morphogenesis?" Cell, 58:803-805 (1989).
Jeong, et al., "The fibronectin-binding domain of transglutaminase", J Biol Chem., 270(10):5654-8 91995).
Kallapur, at al., "The neural cell adhesion molecule (NCAM) heparin binding domain binds to cell surface heparan sulfate proteoglycans," J. Neuro. Res., 33 (4):538-48 (1992).
Kaneda, et al., "Midkine, a heparin-binding growth/differentiation factor, exhibits nerve cell adhesion and guidance activity for neurite outgrowth in vitro,"J. Biochem., 119(6)1150-6 (1996).
Kang, et al., "Selective stimulation of endothelial cell proliferation with inhibition of smooth muscle cell proliferation by fibroblast growth factor-1 plus heparin delivered from glue suspensions," Surgery, 118:280-287 (1995).
Kiguchi, et al., "Altered expression of epidermal growth factor receptor ligands in tumor promoter-treated mouse epidermis and in primary mouse skin tumors induced by an initiation-promotion protocol," Mol. Carcinog., 22(2):73-83 (1998).
Kinosaki, et al., "Identification of heparin-binding stretches of a naturally occurring deleted variant of hepatocyte growth factor (dHGF)," Biochim. Biophys. 1384(1):93-102 (1998).
Kleinman, et al., "The laminins: a family of basement membrane glycoproteins important in cell differentiation and tumor metastases," Vitam. Horn., 47:161-86 (1993).
Lee, et al., "Analysis of affinity and stru ctural selectivity in the binding of proteins to glycosaminoglycans: Development of a sensitive electrophoretic approach," Biochemistry, 88:2768-2772 (1991).
Lin, et al., "Purification and Initial Characterization of Rat B49 Glial Cell Line-Derived Derived Neurotrophic Factor," Journal of Neurochemistry, 63(2):758-768 (1994).

Lopez, et al., "Basic fibroblast growth factor in a porcine model of chronic myocardial ischemia: a comparison of angiographic, echocardiographic and coronary flow parameters," J. Pharmacol. Exp. Ther., 282(1):385-90 (1997).
Lopez, et al., "Local perivascular administration of basic fibroblast growth factor: drug delivery and toxicological evaluation," Drug Metab. Dispos., 24(8):922-4 (1996).
Lorsordo, et al, "Gene therapy for myocardial angiogenesis. Initial clinical results with direct myocardial injection of phVEGF165 as sole therapy for myocardial ischemia," Circulation, 98:2800-2804 (1998).
Ludbrook, et al., "The integrin alphavbeta3 is a receptor for the latency-associated peptides of transforming growth factors betaI and beta3", Biochem J., 369(Pt 2):311-8 (2003).
Luginbuehl, et al., "Localized delivery of growth factors for bone repair" European Journal of Pharmaceutics and Biopharmaceutics, 58:197-208 (2004).
Lyon, et al., "The Interaction of the Transforming Growth Factor-ps with Heparin/Heparan Sulfate is Isoform-specific," The Journal of Biological Chemistry, 272 (29):18000-18006 (1997).
Maeno, et al., "The effect of calcium ion concentration on osteoblast viability, proliferation and differentiation in monolayer and#s=s#culture," Biomaterials, 26:4847-55 (2005).
Martin and Timpl, "Laminin and other basement membrane components," Annu. Rev. Cell.Dev. Biol., 3:57-85 (1987).
Massia, et al., "An RGD spacing of 440 nm is sufficient for integrin alpha V beta 3-mediated fibroblast spreading and 140 nm for focal contact and stress fiber formation," J. Cell. Biol., 114(5):1089-100 (1991).
Maysinger, et al., "Microencapsulated nerve growth factor: effects on the forebrain neurons following devascularizing cortical lesions," Neuroscience Letters, 140:71-74 (1992).
McCaffrey, at al., "Transforming growth factor-beta 1 is a heparin-binding protein: identification of putative heparin-binding regions and isolation of heparins with varying affinity for TGF-beta 1 "J. Cell. Physiol., 152(2):430-40 (1992).
Monsonego, et al., "Factor XIIIa as a nerve-associated transglutaminase", FASEB J., 12(12):1163-71 (1998).
Montgomery, et al., "Human neural cell adhesion molecule L1 and Rat homologue NILE are ligands for integrin a?3," J Cell. Biol, 132:475-485 (1996).
Nehls and Herrmann, "The configuration of fibrin clots determine capillary morphogenesis and endothelial cell migration," Microvascular Research, 51:347-364 (1996).
Nesti, et al., "TGF-betal calcium signaling increases alpha5 integrin expression in osteoblasts", J Orthop Res., 20(5):1042-9 (2002).
Netzel-Arnett, et al., "Sequence specificities of human fibroblast and neutrophil collagenases", J. Biol. Chem., 266:6747-6755(1991).
Nolo, at al., "Developmentally regulated neurite outgrowth response from dorsal root ganglion neurons to heparin-binding growth-associated molecule (HB-GAM) and the expression of HB-GAM in the targets of the developing dorsal root ganglion neurites," Eur. J. Neurosci., 8(8):1658-65 (1996).
Nuss, et al., "An animal model in sheep for biocompatibility testing of biomaterials in cancellous bones", BMC Musculoskeletal Disorders, 7:67 (2006).
Paciorek, et al., "Optimization of fibrin gel for the therapeutic treatment of cerebral aneurysms", Annual fall meeting of the BMES, see poster abstract P2:199, Sep. 26-29, 2007.
Pepper, et al., "Angiogenesis: a paradigm for balanced extracellular proteolysis cell migration and morphogenesis," Enzyme Protein, 49:138-162 (1996).
Poole and Reeve, "Parathyroid hormone—a bone anabolic and catabolic agent," Current Opinion in Pharmacology, 5: 612-7 (2005).
Potts, "Parathyroid hormone: past and present", J Endocrinol., 187(3):311-25 (2005).
Powell, et al., "Controlled Release of nerve growth factor from a polymeric implant," Brain Research 515:309-311 (1990).
Presta, at al., "Structure-function relationship of basic fibroblast growth factor: site-directed mutagenesis of a putative heparin-binding and receptor-binding region," Blochem. Biophys. Res. Commun., 185(3):1098-107 (1992).

(56) References Cited

OTHER PUBLICATIONS

Reddi, "Role of Morphogenetic Proteins in Skeletal Tissue Engineering and Regeneration," Nature Biotechnol., 16:247-252 (1998).
Rixon, et al., "Do the non-catalytic polysaccharide-binding domains and linker regions enhance the biobleaching properties of modular xylanases?" Appl. Microbiol. Biotechnol., 46(5-6): 514-520 (1996).
Rixon, et al., "Parathyroid hormone fragments may stimulate bone growth in ovariectomized rats by activating adenylyl cyclase", J Bone Miner. Res., 9 (8):1179-89 (1994).
Rogers, et al., "Neuron-specific interactions with two neurite-promoting fragments of fibronectin," J. Neurosci., 5(2):369-78 (1985).
Rosengart, at al., "Angiogenesis Gene Therapy. Phase I assessment of direct intramyocardial administration of an adenovirus expressing phVEGF165 cDNA to individuals with clinically significant severe coronary artery disease," Circulation, 100:468-474 (1999).
Rouslahti, et al., "Perspective Series: Cell adhesion in vascular biology", J din Invest, 99:1149-1152 (1997).
Rout, et al., "Transforming growth factor-betal modulates expression of adhesion and cytoskeletal proteins in human peritoneal fibroblasts", Fertil Steril., 78 (1):154-61 (2002).
Sakata, at al "Cross-linking of 02-plasmin inhibitor to fibrin by fibrin-stabilizing factor," J din Invest, 65:290-297 (1980).
Sakiyama, et al., "Incorporation of heparin-binding peptides into fibrin gels enhances neurite extension: an example of designer matrices in tissue engineering," FASEB J 13 (15): 2214-24 (1999).
Sakiyama-Elbert, at al., "Development of fibrin derivatives for controlled release of heparin binding growth factors,"J. Controlled Release, 65(3) 389-402 (2000).
Sakiyama-Elbert, at al., "Development of growth factor fusion proteins for cell-triggered triggered drug delivery" FASEB J., 15:1300-1302(2001).
Sakiyama-Elbert and Hubbell, "Controlled release of nerve growth factor from a heparin-containing fibrin-based cell ingrowth malm" Journal of Controlled Release, 69:149-158 (2000).
Saraph, et al., "Treatment of unicameral calcaneal bone cysts in children", J Pediatr. Orthop, 24(5):568-73 (2004).vbTab.
Schense, et al., "Cross-linking exogenous Afunctional peptiedes into fibrin gels with factor XIIIa," Bioconjug. Chem., 10(1): 75-81 (1999).
Schense, et al., "Enzymatic incorporation of bioactive peptides into fibrin matrices enhances neurite extension" Nature Biotechnology, 18:415-419 (2000).
Schilling, et al., "Osteoclasts and biomaterials," European Journal of Trauma, 2:107-13 (2006).
Schroeder-Tefft et al., "Collagen and heparin matrices for growth factor delivery," Journal of Controlled Release, 49:291-298 (1997).
Schumacher, et al., "Induction of neoangiogenesis in ischemic myocardium by human growth factors," Circulation, 97:645-650 (1998).
Seibel, et al., Transfection of mitochnondria: strategy towards a gene therapy of mitochondrial DNA diseases, Nucleic Acids Res., 23(1):10-7 (1995).
Sellke, et al., "Basic FGF enhances endothelium-dependent relaxation of the collateral-perfused coronary microcirculation," Am. J. Physiol. 267(4 Pt 2):H1303-11 (1994).
Shin, et al., "Expression of EphrinB2 identifies a stable genetic difference between arterial and venous vascular smooth muscle as well as endothelial cells, and of adult neovascularization," Developmental Biology, 230:139-150 (2001).
Shireman, et al., "Modulation of vascular cell growth by local cytokine delivery from fibrin glue suspensions," J Vase Surg, 19:852-62 (1999).
Sierra,"Fibrin sealant adhesive systems: Review of their chemistry, material properties, and clinical applications", J Biomaterials Applications, 7:309-52 (1993).
Smith, et al., "Rapid Identification of Highly Active and Selective Substrates for Stromelysin and Matrilysin Using Bacteriophage Peptide Display Libraries", J. Biol. Chem., 270:6440-6449 (1995).
Spillman, et al., "Defining the interleukin-8-binding domain of heparan sulfate,"J. Biol. Chem., 273(25):15487-93 (1998).
Steffen, et al., "Characterization of cell-associated and soluble forms of connective tissue growth factor (CTGF) produced by fibroblast cells in vitro," Growth Factors, 15 (3):199-213 (1998).
Stein, et al., "Eph receptors discriminate specific ligand oligomers to determine alternative signaling complexes, attachment, and assembly responses," Genes & Development, 12:667-678 (1998).
Studier, et al., "Use of T7 RNA polymerase to direct expression of cloned genes," Methods Enzymol 185:60-89 (1990).
Takagi and Doolittle, "Amino acid sequence studies on the alpha chain of human fibrinogen. Location of four plasmin attack points and a covalent cross-linking site", Biochem., 14:5149-5156 (1975).
Takeshita, et al., "Therapeutic Angiogenesis. A single intraarterial bolus of vascular endothelial growth factor augments revascularization in a rabbit ischemic hind limb model," J din Invest, 93:662-670 (1994).
Tashiro, et al., "A synthetic peptide containing the IKVAV sequence from the A chain of laminin mediates cell attachment, migration, and neurite outgrowth," J. Biol. Chem., 264 (27):16174-82 (1989).
Tessler, at al, "Heparin modulates the interaction of VEGF165 with soluble and cell associated flk-1 receptors," J. Biol. Chem., 269(17):12456-61 (1994).
Thompson, et al., "Site-directed neovessel formation in vivo," Science. 241:1349-1352 (1988).
Tyler-Cross, et al., "Heparin binding domain peptides of antithrombin III: analysis by isothermal titration calorimetry and circular dichroism spectroscopy," Protein Sci., 3(4):620-7 (1994).
Usia, et al., "Propolypeptide of von Willebrand factor serves as a substrate for factor XIIIa and is cross-linked to laminin", J Biol Chem., 268(17):12311-6 (1993).
Wang, at al., "Molecular distinction and angiogenesis interaction between embryonic arteries and veins revealed by ephrin-B2 and its receptor Eph-B4," Cell, 93:741-753 (1998).
Weatherford, at al., "Vascular endothelial growth factor and heparin in a biologic glue promotes human aortic endothelial cell proliferation with aortic smooth muscle cell inhibition," Surgery, 433-439 (1996).
Yamada, "Adhesive recognition sequences," J. Biol. Chem., 266(20):12809-12 (1991).
Yamada, at al., "Characterization of fibronectin interactions with glycosaminoglycans and identification of active proteolytic fragments", J Biol Chem., 255(13):6055-63 (1980).
Yanish-Perron, at al., "Improved M13 phage cloning vectors and host strains: nucleotide sequences of the M13mp18 and pUC19 vectors," Gene, 33(1):103-19 (1985).
Zisch, et al., "Covalently conjugated VEGF-fibrin matrices for endothelialization" Journal of Controlled Release, 72:101-113 (2001).
Zucker and Katz, "Platelet factor 4: production, structure, and physiologic and immunologic action," Proc. Soc. Exp. Biol. Med., 198(2):693-702 (1991).

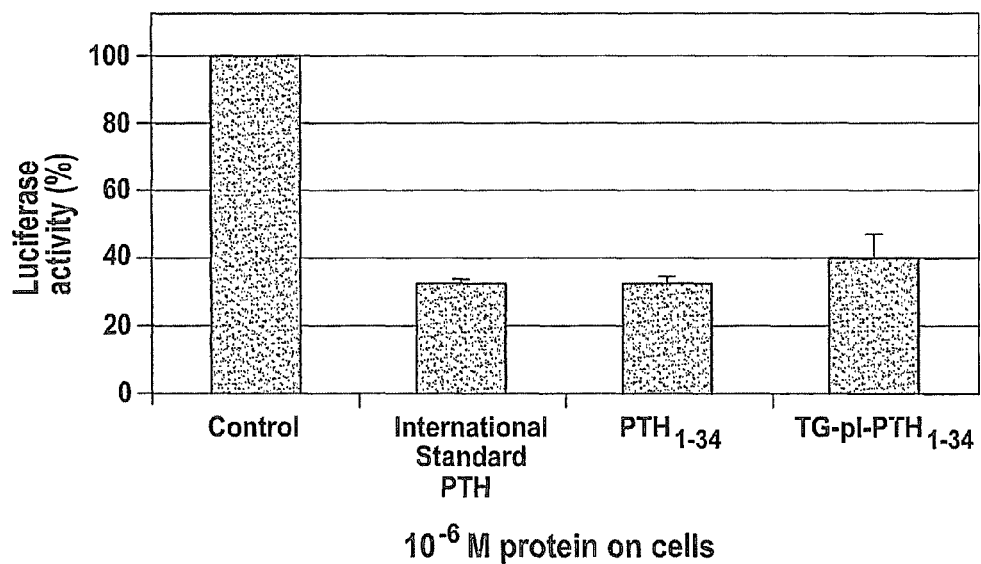
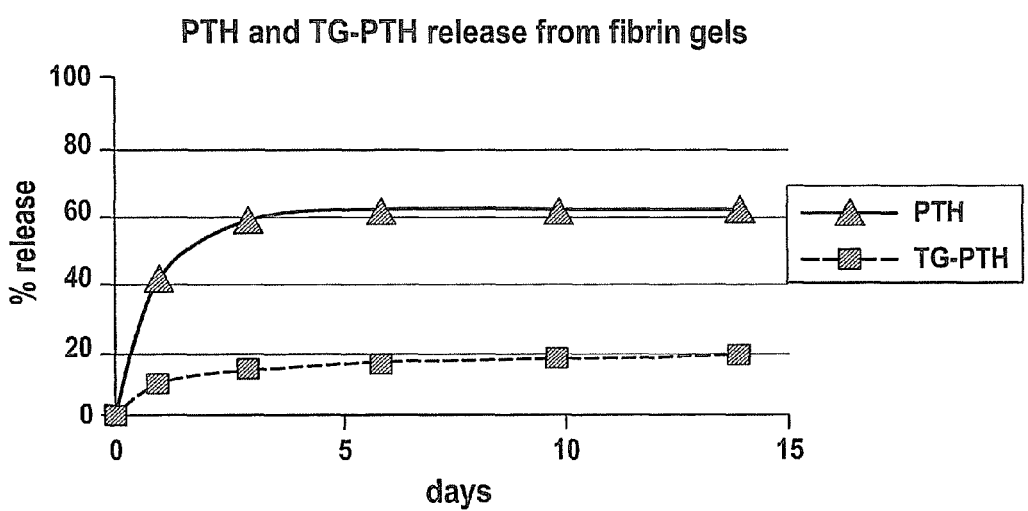

SEQUENCE LISTING

```
<160> NUMBER OF SEQ ID NOS: 21

<210> SEQ ID NO 1
<211> LENGTH: 5
<212> TYPE: PRT
<213> ORGANISM: Homo sapiens

<400> SEQUENCE: 1

Tyr Ile Gly Ser Arg
1               5

<210> SEQ ID NO 2
<211> LENGTH: 7
<212> TYPE: PRT
<213> ORGANISM: Homo sapiens

<400> SEQUENCE: 2

Asn Gln Glu Gln Val Ser Pro
1               5

<210> SEQ ID NO 3
<211> LENGTH: 5
<212> TYPE: PRT
<213> ORGANISM: Homo sapiens

<400> SEQUENCE: 3

Leu Arg Gly Asp Asn
1               5

<210> SEQ ID NO 4
<211> LENGTH: 5
<212> TYPE: PRT
<213> ORGANISM: Homo sapiens

<400> SEQUENCE: 4

Pro Asp Gly Ser Arg
1               5
```

```
<210> SEQ ID NO 5
<211> LENGTH: 5
<212> TYPE: PRT
<213> ORGANISM: Homo sapiens

<400> SEQUENCE: 5

Ile Lys Val Ala Val
1               5

<210> SEQ ID NO 6
<211> LENGTH: 10
<212> TYPE: PRT
<213> ORGANISM: Homo sapiens

<400> SEQUENCE: 6

Arg Asn Ile Ala Glu Ile Ile Lys Asp Ile
1               5                   10

<210> SEQ ID NO 7
<211> LENGTH: 5
<212> TYPE: PRT
<213> ORGANISM: Homo sapiens

<400> SEQUENCE: 7

Gly Ala Lys Asp Val
1               5

<210> SEQ ID NO 8
<211> LENGTH: 4
<212> TYPE: PRT
<213> ORGANISM: Homo sapiens

<400> SEQUENCE: 8

Lys Lys Lys Lys
1

<210> SEQ ID NO 9
<211> LENGTH: 16
<212> TYPE: PRT
<213> ORGANISM: Homo sapiens

<400> SEQUENCE: 9

Tyr Arg Gly Asp Thr Ile Gly Glu Gly Gln Gln His His Leu Gly Gly
1               5                   10                  15

<210> SEQ ID NO 10
<211> LENGTH: 6
<212> TYPE: PRT
<213> ORGANISM: Homo sapiens

<400> SEQUENCE: 10

Leu Ile Lys Met Lys Pro
1               5

<210> SEQ ID NO 11
<211> LENGTH: 6
<212> TYPE: PRT
<213> ORGANISM: Homo sapiens

<400> SEQUENCE: 11

Asn Phe Lys Ser Gln Leu
1               5

<210> SEQ ID NO 12
<211> LENGTH: 8
<212> TYPE: PRT
```

```
<213> ORGANISM: Homo sapiens
<220> FEATURE:
<221> NAME/KEY: Acetylated
<222> LOCATION: (1)..(1)

<400> SEQUENCE: 12

Gly Pro Leu Ala Leu Thr Ala Leu
1               5

<210> SEQ ID NO 13
<211> LENGTH: 6
<212> TYPE: PRT
<213> ORGANISM: Homo sapiens
<220> FEATURE:
<221> NAME/KEY: Acetylated
<222> LOCATION: (1)..(1)

<400> SEQUENCE: 13

Pro Phe Glu Leu Arg Ala
1               5

<210> SEQ ID NO 14
<211> LENGTH: 5
<212> TYPE: PRT
<213> ORGANISM: Homo sapiens

<400> SEQUENCE: 14

Glx Ala Ala Phe Ala
1               5

<210> SEQ ID NO 15
<211> LENGTH: 8
<212> TYPE: PRT
<213> ORGANISM: Homo sapiens

<400> SEQUENCE: 15

Gly Pro Leu Gly Ile Ala Gly Pro
1               5

<210> SEQ ID NO 16
<211> LENGTH: 8
<212> TYPE: PRT
<213> ORGANISM: Homo sapiens

<400> SEQUENCE: 16

Pro His Tyr Gly Arg Ser Gly Gly
1               5

<210> SEQ ID NO 17
<211> LENGTH: 9
<212> TYPE: PRT
<213> ORGANISM: Homo sapiens

<400> SEQUENCE: 17

Pro Gly Ser Gly Arg Ser Ala Ser Gly
1               5

<210> SEQ ID NO 18
<211> LENGTH: 4
<212> TYPE: PRT
<213> ORGANISM: Homo sapiens

<400> SEQUENCE: 18

Tyr Lys Asn Arg
1
```

```
<210> SEQ ID NO 19
<211> LENGTH: 46
<212> TYPE: PRT
<213> ORGANISM: Artificial sequence
<220> FEATURE:
<223> OTHER INFORMATION: Modified Parathyroid hormone (PHT), comprisig
      amino acids 1-34 of native PTH as well as a transglutaminase
      substrate domain and a plasmin-degradable sequence

<400> SEQUENCE: 19

Asn Gln Glu Gln Val Ser Pro Leu Tyr Lys Asn Arg Ser Val Ser Glu
1               5                   10                  15

Ile Gln Leu Met His Asn Leu Gly Lys His Leu Asn Ser Met Glu Arg
            20                  25                  30

Val Glu Trp Leu Arg Lys Lys Leu Gln Asp Val His Asn Phe
        35                  40                  45

<210> SEQ ID NO 20
<211> LENGTH: 42
<212> TYPE: PRT
<213> ORGANISM: Artificial sequence
<220> FEATURE:
<223> OTHER INFORMATION: Modified Parathyroid hormone (PHT), comprisig
      amino acids 1-34 of native PTH as well as a transglutaminase
      substrate domain

<400> SEQUENCE: 20

Asn Gln Glu Gln Val Ser Pro Leu Ser Val Ser Glu Ile Gln Leu Met
1               5                   10                  15

His Asn Leu Gly Lys His Leu Asn Ser Met Glu Arg Val Glu Trp Leu
            20                  25                  30

Arg Lys Lys Leu Gln Asp Val His Asn Phe
        35                  40

<210> SEQ ID NO 21
<211> LENGTH: 35
<212> TYPE: PRT
<213> ORGANISM: Artificial Sequence
<220> FEATURE:
<223> OTHER INFORMATION: Modified PTH

<400> SEQUENCE: 21

Cys Ser Val Ser Glu Ile Gln Leu Met His Asn Leu Gly Lys His Leu
1               5                   10                  15

Asn Ser Met Glu Arg Val Glu Trp Leu Arg Lys Lys Leu Gln Asp Val
            20                  25                  30

His Asn Phe
        35
```

SUPPLEMENTED MATRICES FOR THE REPAIR OF BONE FRACTURES

CROSS-REFERENCE TO RELATED APPLICATIONS

This application is a continuation in part of U.S. Ser. No. 11/327,214 filed Jan. 6, 2006, which claims priority to U.S. Ser. No. 60/641,715, filed Jan. 6, 2005 and U.S. Ser. No. 60/642,644 filed Jan. 10, 2005. The disclosures of these applications are herein incorporated by reference.

REFERENCE TO SEQUENCE LISTING

The Sequence Listing submitted Jun. 23, 2011 as a text file named "KUROS_131_CIP_ST25.txt", created on Jun. 22, 2011, and having a size of 4,482 bytes is hereby incorporated by reference pursuant to 37 C.F.R. §1.52(e)(5).

FIELD OF THE INVENTION

The present application relates to supplemented matrices and uses thereof for the repair and healing of bone fractures.

BACKGROUND OF THE INVENTION

In both Europe and the United States an estimated 5 to 6 million people sustain bone fractures each year due to trauma, sports- or activity-related injuries or osteoporosis. Most of these injuries may be treated with manual reduction and external fixation (e.g. a cast). However approximately 20 to 25% of fractures require hospitalization, usually with open surgical procedures.

With respect to fractures, bone fragments do not have to separate for the injury to be classified as a fracture. In some cases the periosteum holds the bone fragments in their original anatomical position. In other cases, the fracture causes the limb to bend, tearing the periosteum or even the surrounding skin and muscle tissue. In still other cases, as is often the case with high-velocity missile injuries or serious accidents, large portions of bone are fragmented or even removed from its original location. The primary goals of fracture treatments are sound union and the restoration of bone function without an outcome of deformity. Obtaining these goals quickly is an increasingly important concern due to disability issues and cost-containment. In a significant part of the patient population both goals, i.e. sound unions and fast restoration of bone function, are at risk due to the patient's age and/or general health condition, and/or the type and/or location of fracture. In particular, in case of osteoporotic patients, the risk of non-unions and increased healing times is high. As a disease of the skeleton, osteoporosis is characterised by low bone mass and the structural deterioration of bone tissue leading to increased bone fragility, increased healing times and the occurrence of non-union.

Bone grafts and bone graft substitutes are widely used in many orthopaedic procedures to treat problems associated with bone loss, delayed union and non-union fractures or as an implant fixation material. In case of severe and complicated fractures, bone graft and bone graft substitutes are used to fill the bone voids and assist the fracture union process after the fracture is stabilized with hardware. Bone grafting materials may be autogenic, allogenic, xenogenic, demineralised bone matrix (DBM), of synthetic origin or mixtures thereof. Bone grafting materials can be classified into materials with osteoconductive, osteoinductive and osteogenic properties. Osteoconductive materials do not create bone; rather they simulate the migration of nearby living bone cells into the material. Osteoinductive materials stimulate the patient's own system to generate bone tissue. Osteogenic materials directly create bone tissue either by stimulating the proliferation of osteoblasts or promoting mesenchymal stem cells to generate bone tissue. Some materials exhibit more than one of the described properties.

Bone autografts are usually harvested from the iliac crest. In spite their advantage of being biocompatible, safe, of a vascularized composition and exhibiting osteoinductive properties, the disadvantages are major. Autografts require a second operation which may lead to postoperative complications which include blood-loss, infections and pain. Autografts are costly due to longer hospital stays and operation time. The supply of autografts per patient is limited, and the post operative pain after harvesting of autogenic material is often higher than the bone fracture itself In spite of the disadvantages, autograft is considered the "gold standard" in terms of bone grafting materials. Laurencin, et al. *Expert Review Medical Devices* 1:49-57 (2006). Allografts are minimally osteoinductive, there is only limited supply, and they pose on the patient the risk of infections due to host pathogens.

Synthetic bone graft materials are developed as an "off-the-shelf" alternative to autogenic bone grafting material. Synthetic bone graft substitutes include ceramic materials and self-setting polymers such as hydroxyapatite and polymethylmethacrylate, collagen, tricalciumphosphate, calcium sulfates and calcium-phosphates, that mimic properties of human bone. However, these materials show poor handling properties and a lack of osteoinductive properties.

In recent years efforts have been made to develop bone graft substitutes which show osteoinductive properties as a true "off-the-shelf alternative" to autografts. DBM is one example of an osteoinductive bone graft substitute. However DBM as an allogenic material faces the same drawbacks like allogenic bone. Other examples are Stryker Corp.'s OP-1® (recombinantly produced bone morphogenic protein 7 (BMP 7) in a collagen matrix) or Medtronic Sofamor Danek's INFUSE® (bone graft substitute material using recombinantly produced BMP2 from collagen sponges). Apart from the expensive and lengthy production process of the BMPs, the proteins in both products are delivered from a collagen matrix in high concentrations. However, collagen matrices from bovine origin carry all the risks of xenogenic materials and show poor handling properties in the surgical procedure, e.g. they are not moldable to closely fit to the shape of the injury site, and the high concentration of BMPs delivered to the body can lead in some of the patients to calcification of organs or to bone formation in other parts of the body.

The N-terminal 34 amino acid domain of the human parathyroid hormone ($PTH_{1-34}$) has been reported to be biologically equivalent to the full length hormone. Parathyroid hormone 1-34 and its mode of action have been first reported in U.S. Pat. No. 4,086,196 to Tregear. $PTH_{1-34}$ is known to be a fully active truncated version of parathyroid hormone which does not have disulfide bonds or significant tertiary structure. It contains a moderate secondary structure, including several alpha helices. Many clinical studies have been carried out using systemically administered parathyroid hormone to increase the overall bone mass in patients with osteoporosis, with the majority requiring daily injections of parathyroid hormone or $PTH_{1-34}$ alone, or in combination with other actives, for many months. More details about PTH and $PTH_{1-34}$ are described in WO 03/052091, the content thereof being incorporated herein by reference. Other truncated versions of parathyroid hormone with biological activity include parathyroid hormone 1-25 ($PTH_{1-25}$), 1-31 ($PTH_{1-31}$) and 1-38 ($PTH_{1-38}$).

While much work has been done studying the systemic effects of PTH, the local administration of PTH has barely been explored. WO 03/052091 describes matrices for local administration of PTH. Specifically, WO 03/052091 describes parathyroid hormone as being covalently attached to synthetic and natural matrices, in particular fibrin or polyethyleneglycol matrices, for local administration and release at the site of need in a controlled fashion.

However, WO 03/052091 does not describe methods for the healing bone fractures, in particular severe bone fractures, like repair of fractures at risk of becoming delayed unions or non-unions.

It is therefore, an object of the present invention to provide a matrix which is suitable for the local repair of bone fractures.

It is further an object of the present invention to provide a method for repairing bone fractures.

SUMMARY OF THE INVENTION

It has been found that a matrix containing PTH ("supplemented matrices") can be used to deliver PTH locally to the site of a bone fracture to enhance healing of the fracture. Enhancing of fracture healing can occur timewise, i.e. that the fracture heals faster than in the absence of the supplemented matrix, or performance wise, that the fracture either heals as well as if the gold standard is applied, which is currently autograph, or that the fracture heals at all which without treatment would not heal. Preferably the PTH is releasably incorporated in the matrix and the supplemented matrix is applied to or formed at the site of the fracture. In a preferred embodiment the PTH is the only peptide or proteinaceous bioactive factor in the matrix with bone forming potential. Thus the healing effect is not the result of a combined local effect with other peptides or proteins being delivered from the matrix or systemically. In one embodiment the PTH is covalently bound to the matrix. In a preferred embodiment, the matrix is a fibrin matrix or a matrix made of synthetic precursor components such as functionalized (poly)alkyleneoxide oligomers or polymers. The parathyroid hormone can be $PTH_{1-84}$ (native), $PTH_{1-38}$, $PTH_{1-34}$, $PTH_{1-31}$, or $PTH_{1-25}$, or any modified or allelic versions of PTH exhibiting properties, i.e. bone formation, similar to the foregoing ("PTH"). Preferably the PTH is $PTH_{1-34}$. In a preferred embodiment, the PTH is provided as a fusion peptide ("PTH fusion peptide") containing at least two domains wherein the first domain comprises PTH and the second domain comprises a covalently crosslinkable substrate domain able to crosslink to the matrix during or after its formation.

In one embodiment, the supplemented fibrin matrix is formed from a formulation comprising (i) a composition suitable of forming a fibrin matrix containing fibrinogen and thrombin and (ii) PTH in a range of between 0.01 to 2 mg PTH/mL fibrin matrix, which is suitable for the healing of bone fractures. Optionally granular calcium containing minerals, like hydroxyapatite or tricalciumphosphates can be incorporated in the supplemented matrix, preferably to add load bearing characteristics to the matrix.

A kit comprising the above formulation is also provided, wherein at least one of the components suitable of forming a matrix is stored separately from the other components for forming the matrix.

The formulations and supplemented matrices are preferably used for healing of bone fractures, in particular for bone fractures with a risk of becoming delayed unions or non-unions. The supplemented matrix also showed excellent healing effects in fractures which are primarily caused by osteoporosis. Preferred indications include fractures of the wrist (distal radius fractures), long bone fractures, like fractures of the tibia, femur, fibula, radius, uln, humerus, hip, and/or vertebra fractures.

BRIEF DESCRIPTION OF THE DRAWINGS

FIG. 1 shows the bioactivity of PTH variants. Cells transfected with a reporter gene linked to a promoter for a PTH receptor were treated with equal amounts of either $PTH_{1-34}$, TG-pl-$PTH_{1-34}$ (described hereinafter) or the international 84 amino acid standard PTH. The inhibition of expression of the luciferase reporter gene was measured and compared to transfected cells that were not exposed to PTH in solution (control).

FIG. 2 shows the results of a PTH release assay from a fibrin matrix.

DETAILED DESCRIPTION OF THE INVENTION

I. Definitions

Figure 3:
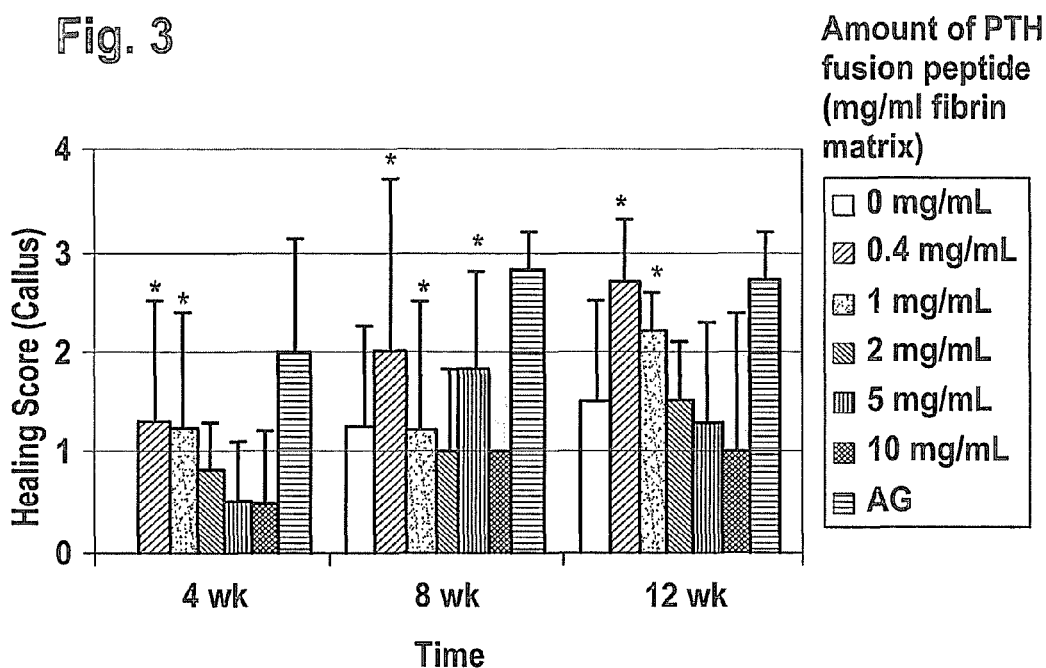
FIG. 3 shows the results of a stability test of segmental tibial defects upon treatment with the supplemented matrix, presented as the score of healing.

A "fracture" is defined as a discontinuity in the bone structure usually resulting from excess mechanical force or injury, or as a result of certain medical conditions that weaken bone, like osteoporosis and bone cancer. In particular, a fracture is a discontinuity in the cortical bone structure.

A "complete fracture" is defined by a discontinuity, or break, that occurs across the entire bone structure, creating two or more distinct bone segments.

"Autograft" refers to any tissue or bone that is harvested from one part of the patient's body to be used at the injury site i.e., a second site.

"Allografts" are bone tissue taken from various locations in a human cadaver body, which can be machined with different structures and into different shapes.

"Adhesion site or cell attachment site" as generally used herein refers to a peptide sequence to which a molecule, for example, an adhesion-promoting receptor on the surface of a cell, binds. Examples of adhesion sites include, but are not limited to, the amino acid RGD sequence from fibronectin, and the YIGSR (SEQ ID NO: 1) sequence from laminin. Adhesion sites can be optionally incorporated into the matrix by including a substrate domain crosslinkable to the fibrin matrix.

"Biological activity" as generally used herein refers to functional events mediated by a protein of interest. In some embodiments, this includes events assayed by measuring the interactions of a polypeptide with another polypeptide. It also includes assaying the effect which the protein of interest has on cell growth, differentiation, death, migration, adhesion, interactions with other proteins, enzymatic activity, protein phosphorylation or dephosphorylation, transcription, or translation.

"Calcium mineral" as generally used herein refers to substances that contain calcium ions. An example of a calcium mineral is hydroxyapatite ($Ca_5[(OH)(PO_4)_3]$), which is the main component of teeth and bones.

"Cross-linking" as generally used herein means the formation of covalent linkages.

"Delayed union" as generally used herein means a bone fracture that has not healed within 3-4 months, i.e. a time span that is considered adequate for normal bone healing. Delayed union generally indicates that union of the bone fragments is slow but will eventually occur with or without additional surgical or non-surgical intervention. However, in some cases a delayed union may progress to a non-union.

"Fibrin matrix" as generally used herein means the product of a process in which the precursor components, fibrinogen and thrombin partially or fully crosslink in the presence of a calcium source and Factor XIIIa. The crosslinked fibrin precursor components, even when only partially crosslinked, form a three-dimensional network.

"Matrix" as generally used herein refers to a material intended to interface with biological systems to treat, augment, or replace any tissue or function of the tissue depending on the material either permanently or temporarily. The matrix can serve as a delivery device for PTH incorporated therein and/or as a cell-ingrowth matrix. The matrices described herein are preferably formed from liquid precursor components which are able to form a scaffold in the body at the site of need. The terms "matrix", "gel" or biomaterials are used synonymously herein. The terms "matrix" and "gel" refer to the composition formed after the precursor components are mixed together. Thus the terms "matrix" and "gel" encompass partially or fully crosslinked polymeric networks. They may be in the form of a liquid, semi-solid, such as a paste, or a solid. Depending on the type of precursor materials, the matrix may be swollen with water but not dissolved in water, i.e. form a hydrogel which stays in the body for a certain period of time.

"Naturally occurring precursor components or polymers" as generally used herein refers to molecules which could be found in nature.

"Non-union" as generally used herein means a bone fracture that does not heal within 6 to 9 months following injury (depending on the type and location of fracture) in monthly radiographic studies.

"PTH" as used herein includes the human sequence of $PTH_{1-84}$ and all truncated, modified and allelic versions of PTH which exhibit bone formation properties, in particular when incorporated (preferably covalently bound) in a fibrin matrix. Preferred truncated versions of PTH are $PTH_{1-38}$, $PTH_{1-34}$, $PTH_{1-31}$ or $PTH_{1-25}$. Most preferred is $PTH_{1-34}$. Preferably, the PTH is human PTH, although PTH from other sources, such as bovine PTH, may be suitable. "PTH" as used herein and if not otherwise indicated, is used as a general term for all versions of PTH, and also includes PTH fusion peptides.

"PTH fusion peptide" as generally used herein refers to a peptide which contains at least a first and a second domain. One domain contains a PTH, preferably $PTH_{1-34}$ and the other domain contains a substrate domain crosslinkable to a matrix during or after its formation. The nature of the crosslinkable substrate domains is dependent of the matrix or matrix precursor component the PTH fusion peptide shall crosslink with. An enzymatic or hydrolytic degradation site can also be present between the first and the second domain.

"Periosteum" as used herein means the outer covering of the bone (with the exception of those portions that form a joint structure) which contains the vasculature that nourishes the bone tissue.

"Physiological" as generally used herein means conditions as they can be found in living vertebrates. In particular, physiological conditions refer to the conditions in the human body such as temperature and pH. Physiological temperatures mean in particular a temperature range of between 35° C. to 42° C., preferably around 37° C.

"Healing of bone fracture" as generally used herein means formation of new bone tissue between the broken ends of bone that restores anatomy and mechanical function of the broken bone ("bridging"). Specifically it means that the gap in the cortical bone is bridged by new bone and that the fracture lines in the substance of the bone have disappeared as assessed radiologically by computed tomography (CT) analysis or X-ray. For humans the restoration of function is commensurate with the patient able to either weight bear, if the previously fractured bone is in the lower limb, or to achieve mechanical strength such as grip strength or normal flexion/extension in the upper limb. In animals, mechanical testing and histological analysis of the new bone has to show good quality of bone tissue.

"Supplemented Matrices" or "biomaterial" as generally used herein means a matrix having PTH incorporated therein.

II. Supplemented Matrices

Supplemented matrices comprising PTH releasably incorporated therein, are described herein. The PTH is incorporated into the matrix either through covalent linkage to the matrix or through non-covalent interaction with the matrix. These supplemented matrices decrease the time of bone healing compared to autograft, and/or trigger healing of bone fractures, which otherwise would not heal, or, showed new bone formation to a lesser degree in the absence of the supplemented matrix. The matrices are biocompatible and biodegradable and can be formed in vitro or in vivo, at the time of implantation. PTH can be incorporated into the matrices with full retention of its bioactivity. PTH can be releasably incorporated, using techniques that provide control over how and when and to what degree the PTH is released using the matrix as a controlled release vehicle to heal bone fractures.

A. Matrix Materials

For tissue repair or regeneration, cells must migrate into a wound bed, proliferate, express matrix components or form extracellular matrix, and form a final tissue shape. Multiple cell populations must often participate in this morphogenetic response, frequently including vascular and nerve cells. Matrices have been demonstrated to greatly enhance, and in some cases have been found to be essential, for this to occur.

Approaches have been made in developing matrices from natural or synthetic origins or a mixture of both. The fibrin matrix, which is described in WO 03/052091, has been found to be suitable a matrix material for the repair of bone fractures.

The matrix can be formed by matrix precursor components assembling through van-der-Waals forces, by ionic or covalent bonds, or adherence by sintering or by combinations thereof. In a preferred embodiment the matrices are formed in situ at the site of application in the body. The matrices can also be pre-formed outside the body and further optimized by water uptake, i.e. swelling, such like collagen sponges. In a preferred embodiment the matrices formed have a network with sufficient inter-polymer spacing to allow for in-growth or migration into the matrix of cells.

In one embodiment the matrix is formed from proteins, preferably proteins naturally present in the patient into which the matrix is to be implanted. A particularly preferred matrix protein is fibrin, although matrices made from other proteins, such as collagen and gelatine can also be used. Polysaccharides and glycoproteins may also be used to form the matrix. In another embodiment the matrix can be formed from synthetic polymers, such as functionalized polyoxyalkylenes, such as polyethyleneoxide or block copolymers of polyethylenoxides and polypropyleneoxides.

In still another embodiment, the matrix can be formed from ceramics, i.e. inorganic materials, like hydroxyapatite, tricalciumphosphate or combinations thereof, calcium sulphate or bioglass ($SiO_2$, $Na_2O$, $CaO$ and $P_2O_5$).

(i) Fibrin Matrices

Fibrin is a natural material which has been reported for several biomedical applications. Matrices made from fibrin have been described as material for cell in-growth matrices in U.S. Pat. No. 6,331,422 to Hubbell et al. Fibrin has been used in sealants because of its ability to bind to many tissues and its natural role in wound healing. Some specific applications include use as a sealant for vascular graft attachment and heart valve attachment. Additionally, these matrices have been used as drug delivery devices, and for neuronal regeneration. Although fibrin matrices provide a solid support for tissue regeneration and cell in-growth, there are few active sequences in the monomer that directly enhance these processes.

Fibrin Structure and Matrix Formation In Vivo

Fibrinogen consists of two tripeptide units with $\alpha\beta\gamma$ structure. The complete molecule has an $\alpha\alpha'$, $\beta\beta'$ and $\gamma\gamma'$ subunit configuration. The two tripeptide structures are covalently linked by disulfide bonds. Devlin, in Textbook of Biochemistry, $3^{rd}$ ed. Wiley-Liss, MY 1992, page 968. The process by which fibrinogen is polymerized into fibrin has also been characterized. Initially, a protease cleaves the dimeric fibrinogen molecule at the two symmetric sites. There are several possible proteases than can cleave fibrinogen, including thrombin, peptidase, and protease III, and each one severs the protein at a different site. Thrombin converts fibrinogen to fibrin monomers by cleaving fibrinopeptides A (16 amino acid residues) and B (14 amino acid residues) from the N-terminal ends of the $A\alpha$ and $B\beta$ chains, respectively. Smith, *Biochemistry J.*, 185(i):1-11 (1980). Once the fibrinogen is cleaved, a self-polymerization step occurs in which the fibrinogen monomers come together and form a non-covalently crosslinked polymer gel. This self-assembly happens because binding sites become exposed after protease cleavage occurs. Once they are exposed, these binding sites in the centre of the molecule can bind to other sites on the fibrinogen chains, which are present at the ends of the peptide chains. In this manner, a polymer network is formed. Factor XIIIa, a transglutaminase activated from Factor XIIIa by thrombin proteolysis, may then covalently crosslink the polymer network. Other transglutaminases exist and may also be involved in covalent crosslinking and grafting to the fibrin network.

Degradation of Fibrin Matrices In Vivo

Once a crosslinked fibrin matrix is formed, the subsequent degradation is tightly controlled. One of the key molecules in controlling the degradation of fibrin is $\alpha2$-plasmin inhibitor. This molecule acts by crosslinking to the a chain of fibrin through the action of Factor XIIIa. By attaching itself to the matrix, a high concentration of inhibitor can be localized to the matrix. The inhibitor then acts by preventing the binding of plasminogen to fibrin and inactivating plasmin. The $\alpha2$-plasmin inhibitor contains a glutamine substrate. The exact sequence has been identified as NQEQVSPL (SEQ ID NO: 2), with the first glutamine being the active amino acid for crosslinking.

Precursor Components for Forming Fibrin Matrices

The fibrin matrix is preferably formed from two precursor components which can be in the form of solutions. The first precursor component, typically in form of a solution, contains fibrinogen, preferably in a concentration range from 10 to 130 mg fibrinogen per milliliter precursor solution, more preferably from 30 to 120 mg fibrinogen per milliliter precursor solution, even more preferably from 50 to 110 mg fibrinogen per milliliter precursor solution, and most preferably from 60 to 90 mg fibrinogen per milliliter precursor solution. If thrombin has to be added to form the matrix, the second precursor component, also typically in form of a solution, contains thrombin, preferably in a concentration range from 1 to 10 I.U. thrombin per milliliter precursor solution, more preferably from 2.5 to 6.5 I.U. thrombin per milliliter precursor solution, most preferably from 3 to 5 I.U. thrombin per milliliter precursor solution. Additionally a calcium ion source is in one of the precursor solutions. The calcium ion source is preferably $CaCl_2*2H_2O$ in a concentration range from 1 to 10 mg per ml precursor solution, even more preferably from 4 to 7 mg per ml precursor solution, most preferably from 5 to 6 mg per ml precursor solution. Optionally, an enzyme capable of catalyzing the matrix formation, like Factor XIIIa, is added to a precursor solution. Preferably, Factor XIIIa is present in a concentration range from 0.5 to 100 I.U. per milliliter precursor solution, more preferably from 1 to 60 I.U. per milliliter precursor solution, and most preferably from 1 to 10 I.U. per milliliter precursor solution. This composition does not take into account any water used to wet any potential granules before mixing into fibrin matrix since the water stays in the pores of the granules throughout the process of matrix formation. Consequently, water used to wet the granules does not have any dilutive effect on the fibrinogen and thrombin concentration in the fibrin matrix. I.U. stands for one international unit of thrombin and is defined as the activity contained in 0.0853 mg of the First International Standard of Human Thrombin.

Fibrin Matrix Composition

Depending on the indication and substances mixed into the fibrin matrix the concentration of thrombin might vary. In one preferred embodiment, the polymerized fibrin matrix contains fibrin in a range of 5 to 65 mg per milliliter fibrin matrix, more preferably 15 to 60 mg per milliliter fibrin matrix, even more preferably from 25 to 55 mg per milliliter fibrin matrix, and most preferably 30 to 45 mg per milliliter fibrin matrix.

(ii) Synthetic Matrices

Crosslinking reactions for forming synthetic matrices for application in the body include (i) free-radical polymerization between two or more matrix material precursor components containing unsaturated double bonds, as described in Hern et al., *J. Biomed. Mater. Res.* 39:266-276 (1998), (ii) nucleophilic substitution reactions such as between a precursor component including an amine group and a precursor component including a succinimidyl group as disclosed in U.S. Pat. No. 5,874,500 to Rhee et al., (iii) condensation and addition reactions, and (iv) Michael type addition reactions between a matrix material precursor component comprising strong nucleophile and a matrix material precursor component comprising conjugated unsaturated group or bone (as a strong electrophile).

Michael type addition reactions are described in WO 00/44808 to Hubbell et al. Michael type addition reactions allow for in situ crosslinking of at least a first and a second matrix material precursor component under physiological conditions in a self-selective manner, even in the presence of sensitive biological materials. When one of the matrix material precursor components has a functionality of at least two, and at least one of the other matrix material precursor components has a functionality greater than two, the system will self-selectively react to form a cross-linked three dimensional matrix. Particularly preferred is the reaction between a matrix material precursor component having a thiol or amine group as the nucleophilic group and a matrix material precursor component having an acrylate or vinyl sulfone groups as electrophilic groups. Preferably, the conjugated unsaturated groups or conjugated unsaturated bonds are acrylates, vinylsulfones, methacrylates, acrylamides, methacrylamides, acrylonitriles, 2- or 4-vinylpyridinium, maleimides, or quinones.

The nucleophilic groups are preferably thiol-groups, amino-groups or hydroxyl-groups. Thiol groups are substantially more reactive than unprotonated amine groups. The most preferred nucleophilic group is the thiol group.

The pH affects the relative reactivity of the nucleophilic groups: the deprotonated thiol is substantially more reactive than the protonated thiol. Therefore, the addition reactions involving a conjugated unsaturation, such as an acrylate or a quinone, with a thiol to convert two matrix material precursor components into a matrix, will often be best carried out most quickly and self-selectively in an alkaline environment, starting at a pH of approximately 8. At pH around 8, most of the thiols on the precursor component are deprotonated (and thus more reactive) and most of the amines of interest are still protonated (and thus less reactive). When a thiol is used as the first precursor molecule, a conjugate structure that is selective in its reactivity for the thiol relative to amines is highly desirable.

In some embodiments, the matrix is a synthetic matrix or a mixed synthetic/natural matrix, and the composition for forming the matrix comprises a matrix material precursor component having strong nucleophilic groups or bonds, and a matrix material precursor component having strong electrophilic groups or bonds.

Synthetic Matrix Material Precursor Components

Suitable first and second matrix material precursor components include proteins, peptides, polyethylene glycol (PEG), polyoxyalkylenes, poly(vinyl alcohol), poly(ethylene-co-vinyl alcohol), poly(acrylic acid), poly(ethylene-co-acrylic acid), poly(ethyloxazoline), poly(vinyl pyrrolidone), poly(ethylene-co-vinyl pyrrolidone), poly(maleic acid), poly(ethylene-co-maleic acid), poly(acrylamide), and poly(ethylene oxide)-co-polypropylene oxide) block copolymers. A particularly preferred matrix material precursor component is based on polyethylene glycol (PEG) such functionalized PEG.

Polyethylene glycol provides a convenient building block. One can readily purchase or synthesize linear or branched PEGs and then functionalize the PEG end groups to introduce either a strong nucleophile, such as a thiol, or a conjugated structure, such as an acrylate or a vinyl sulfone. When these components are either mixed with each other or with a corresponding component in a slightly basic environment, a matrix will be formed by reaction between the first and the second precursor component, i.e. between the thiol and the acrylate or vinylsulfone. A PEG precursor component can be reacted with a non-PEG precursor component, and the molecular weight or hydrophilicity of either component can be controlled to manipulate the mechanical characteristics, the permeability, and the water content of the resulting matrix.

In the formation of matrices, especially matrices that are designed to degrade in vivo, peptides also provide a very convenient building block. It is straightforward to synthesize peptides that contain two or more cysteine residues, and this component can then readily serve as the first matrix precursor component with nucleophilic groups, i.e., thiol groups. For example, a peptide with two free cysteine residues will readily form a matrix when mixed with a PEG tri-vinylsulfone (a PEG having three arms with vinylsulfones at each of its arms) at physiological or slightly higher pH (e.g., 8 to 9). The gelation can also proceed well at even higher pH, but at the potential expense of self-selectivity. When the two liquid precursor components are mixed together, the crosslinking time can be tailored between a few seconds to several minutes to form an elastic gel, consisting of a network of PEG chains, bearing the nodes of the network, with the peptides as connecting links.

The peptides can be selected as protease substrates, so as to make the network capable of being infiltrated and degraded by cells, as is done in a protein-based network, such as in a fibrin matrix. Preferably the sequences in the domains are substrates for enzymes that are involved in cell migration (e.g., substrates for enzymes such as collagenase, plasmin, metalloproteinase (MMP) or elastase), although suitable domains are not limited to these sequences. One particularly useful sequence is a substrate for the enzyme plasmin. The degradation characteristics of the gels can be manipulated by changing the details of the peptide that serves as the crosslinking nodes. One may make a matrix that is degradable by collagenase, but not plasmin, or by plasmin, but not collagenase. Furthermore, it is possible to make the gel degrade faster or slower in response to such an enzyme, simply by changing the amino acid sequence so as to alter the $K_m$ or $k_{cat}$, or both, of the enzymatic reaction. One can thus make a matrix that is biomimetic, in that it is capable of being remodeled by the normal remodeling characteristics of cells. For example, such a study shows substrate sites for the important protease plasmin. The gelation of the PEG with the peptide is self-selective.

Matrices formed from the reaction of precursor components having acrylates as functional groups and precursor components having thiols as functional groups, contain hydrolytically degradable ester bonds. Other matrix types might need the addition of hydrolytic or enzymatic degradable linkages. Having protease substrates incorporated into the matrix can be important when the matrix is formed from matrix precursor components having functional groups like vinylsulfones, which do not lead to linkages that are hydrolytically degradable after reaction with nucleophiles like thiols or amines. Therefore, the incorporation of protease substrates allows the matrix to degrade in the body in all the cases in which the reaction of the matrix material precursor components do not lead to hydrolytically degradable bonds.

The synthetic matrices are operationally simple to form. At least two liquid matrix material precursor components are mixed; one of the liquid components contains a precursor molecule with nucleophilic groups and the other contains the electrophilic groups. Physiological saline can serve as the solvent. Minimal heat is generated by the reaction. Therefore, the gelation can be carried out in vivo or in vitro, in direct contact with tissue, without untoward toxicity. Thus polymers other than PEG may be used either telechelically modified or modified on their side groups.

(iii) Ceramic Matrices

In still another embodiment, the matrix can be formed from ceramics, i.e. inorganic materials, like hydroxyapatite (HA), tricalciumphosphate (TCP) or combinations thereof, calcium sulphate or bioglass ($SiO_2$, $Na_2O$, $CaO$ and $P_2O_5$). For example, a solution containing PTH may be mixed with ceramic granules, such as HA, TCP, or HA/TCP granules, and allowed to equilibrate. After equilibration supernatant may be collected, and the particles may be separated by suitable means, such as centrifugation.

Preferably the PTH is PTH 1-34. A fusion peptide is not needed to attach the PTH to the ceramic matrix. For example, different concentrations of PTH, such as 1, 0.5, 0.25, 0.1, 0.05 mg $PTH_{1-34}$/ml water, were mixed with HA/TCP granules. It was found using UV-Vis spectra, scanned at 280 nm, that approximately 25% of the amount of $PTH_{1-34}$ present in the solution was adsorbed onto the granules, with the maximum amount of $PTH_{1-34}$ on the matrix being 1 mg of PTH on 1 g of matrix (HA/TCP).

B. Cell Attachment Sites

Cells interact with their environment through protein-protein, protein-oligosaccharide and protein-polysaccharide interactions at the cell surface. Extracellular matrix proteins provide a host of bioactive signals to the cell. This dense network is required to support the cells, and many proteins in the matrix have been shown to control cell adhesion, spreading, migration and differentiation. Some of the specific proteins that have been shown to be particularly active include laminin, vitronectin, fibronectin, fibrin, fibrinogen and collagen. Many studies of laminin have been conducted, and it has been shown that laminin plays a vital role in the development and regeneration of nerves in vivo and nerve cells in vitro, as well as in angiogenesis. Some of the specific sequences that directly interact with cellular receptors and cause either adhesion, spreading or signal transduction have been identified.

Laminin, a large multidomain protein, has been shown to consist of three chains with several receptor-binding domains. These receptor-binding domains include the YIGSR (SEQ ID NO: 1) sequence of the laminin B1 chain, LRGDN (SEQ ID NO: 3) of the laminin A chain and PDGSR (SEQ ID NO: 4) of the laminin B1 chain. Several other recognition sequences for cells have also been identified. These include IKVAV (SEQ ID NO: 5) of the laminin A chain and the sequence RNIAEIIKDI (SEQ ID NO: 6) of the laminin B2 chain. Particularly preferred is the RGD sequence from fibronectin.

In a further preferred embodiment peptide sites for cell adhesion are incorporated into the matrix, namely peptides that bind to adhesion-promoting receptors on the surfaces of cells. Such adhesion promoting peptides include those described above. Particularly preferred are the RGD sequence from fibronectin and the YIGSR (SEQ ID NO: 1) sequence from laminin. Cell attachment sites can be included with some of the natural matrices. The incorporation can be accomplished, for example, by mixing a cysteine-containing cell attachment peptide with the precursor molecule including the conjugated unsaturated group, such as PEG acrylate, PEG acrylamide or PEG vinylsulfone. This step may occur shortly, e.g. a few minutes, before mixing with the remainder of the precursor component including the nucleophilic group, such as thiol-containing precursor component. If the cell attachment site does not include a cysteine, it can be chemically synthesized to include one. During this step, the adhesion-promoting peptide will become incorporated into one end of the precursor multiply functionalized with a conjugated unsaturation; when the remaining multi-thiol precursor component is added to the system, a cross-linked network will form.

The concentration of adhesion sites covalently bound into the matrix can influence the rate of cell infiltration. For example, for a given hydrogel, cell adhesion molecules such as RGD can be incorporated into the matrix in an effective concentration to support cell in-growth and cell migration. The preferred concentration range of cell adhesion molecule for example, RGD, is between 0.04 and 0.05 mM and even more preferably 0.05 mM in particular, for a matrix having a water content between equilibrium concentration and 92 weight % after termination of water uptake.

C. PTH

The term "PTH" as used herein includes the human sequence of $PTH_{1-84}$ and all truncated, modified and allelic versions of PTH which exhibit bone formation properties including PTH fusion peptides. Preferred truncated versions of PTH are $PTH_{1-38}$, $PTH_{1-34}$, $PTH_{1-21}$, $PTH_{1-28}$ or $PTH_{1-25}$. Most preferred is $PTH_{1-34}$. Preferably, the PTH is human PTH, although PTH from other sources, such as bovine PTH, may be suitable. The concentration of PTH in the matrix is in a range of between 0.01 to 2 mg PTH/mL-matrix, Preferably the concentration of PTH is in a range of between 0.1 to 1.7 mg/mL-matrix, even more preferably the concentration range is in a range of between 0.3 to 1.5 mg/mL matrix and most preferably in a concentration range of between 0.4 to 1.1 mg/mL-matrix. In a preferred embodiment the matrix is a fibrin matrix. In a preferred embodiment the PTH is the only peptide or proteinaceous bioactive factor in the matrix with bone forming characteristics. Thus the favorable biological response in terms of bone healing can be attributed to the PTH and/or the combination of matrix and PTH and is not due to a combined effect of other peptides or proteins (given locally or systemically) having bone forming properties with the PTH and/or the matrix.

PTH Fusion Peptides

It has been demonstrated that bi-domain peptides, which contain a substrate that is crosslinkable to a matrix or matrix precursor components in one domain and a bioactive peptide sequence, enable the bidomain peptide to be cross-linked to certain matrices during or after its formation and that this bioactive peptide retains its cellular activity in vitro.

In one preferred embodiment the bioactive peptide sequence of that bidomain peptide is PTH (in this context, the definition of PTH does not include the PTH fusion peptide). In case the matrix is a fibrin matrix formed from fibrinogen and thrombin in the presence of Factor XIIIa and a calcium source, the substrate domain is a domain for an enzyme, preferably a substrate domain for a transglutaminase ("transglutaminase substrate domain"), more preferably for a tissue transglutaminase ("tissue transglutaminase substrate domain") and most preferred it is a substrate domain for Factor XIIIa ("Factor XIIIa substrate domain"). Transglutaminases catalyse acyl-transfer reactions between the gamma-carboxamide group of protein bound glutaminyl residues and the epsilon-amino group of lysine residues, resulting in the formation of N-epsilon-(gamma-glutamyl)lysine isopeptide side chains bridges. The amino acid sequence of the PTH fusion peptide can be designed to further contain an enzymatically or hydrolytically degradable site, such that the PTH can be released with little or no modification to the primary structure.

Transglutaminase substrate domains and in particular, Factor XIIIa substrate domains, are suitable to link the PTH fusion peptide to natural matrices, such as fibrin matrices. When used with a fibrin matrix, the degradation site in the PTH fusion peptide is preferably enzymatically degradable, so that the release of the PTH is controlled by cell specific processes, such as localized proteolysis.

The crosslinkable substrate domain may include GAKDV (SEQ ID NO: 7), KKKK (SEQ ID NO: 8), YRGDTIGEGQQHHLGG (SEQ ID NO: 9), or NQEQVSPL (SEQ ID NO: 2).

The most preferred Factor XIIIa substrate domain has an amino acid sequence of NQEQVSPL (SEQ ID NO: 2) and is herein referred to as "TG" and TG-PTH.

The PTH fusion peptide may be produced recombinantly or by chemical synthesis. The PTH 1-34 fusion peptide is preferably produced by chemical synthesis.

Transglutaminase substrate domains suitable for the purposes of the present invention have been described in detail including their amino acid sequences in WO 03/052091, the respective content thereof being incorporated herein by reference.

In a preferred embodiment the Factor XIIIa substrate domain is either directly linked to the $PTH_{1-34}$ or it can include a degradation site between the PTH (first domain) and the transglutaminase substrate domain. Preferably, the transglutaminase substrate domains comprises the NQEQVSP (SEQ ID NO: 2) sequence as the second domain and a YKNR (SEQ ID NO: 18) sequence as the degradation site. As such, the $PTH_{1-34}$ fusion peptide may be incorporated within fibrin during coagulation via a factor XIIIa substrate and released either as $PTH_{1-34}$ or as $PTH_{1-34}$ plus the additional amino acid sequence NR. As such the degradation sites allow the PTH to be released with little or no modification to the primary peptide sequence, which may result in higher activity of the factor. In addition, it allows the release of the factor to be controlled by cell specific processes. This allows factors to be released at different rates within the same material depending on the location of cells within the material. This also reduces the amount of total $PTH_{1-34}$ needed, since its release is controlled by cellular processes. In one possible explanation for the strong healing of the above mentioned bone defects with PTH incorporated and preferably bound to a matrix, it is deemed important that the PTH is administered locally over an extended period of time (i.e. not just a single pulsed dose). This is accomplished by a slow degradation, through either enzymatic cleavage or hydrolytic cleavage of the matrix. When a preosteoblastic cell infiltrates the matrix, it encounters a PTH molecule which induces further proliferation of the preosteoblast as well as synthesis of multiple growth factors crucial for new bone formation. However, if that particular cell does not continue to liberate bound PTH from the matrix, it will not begin to produce interleukin-6, thereby avoiding the later stage catabolic effects on osteoclasts formation. The net result is then higher bone mineral density and net formation of bone matrix. Finally, the therapeutic effects of the peptide are localized to the defect region and are subsequently magnified compared to systemic delivery of the peptide.

Similar mechanism of incorporation, release and healing effects can be observed when the PTH is crosslinked to synthetic matrices.

In case of a synthetic matrices formed by a Michael-type addition reaction from precursor components having conjugated unsaturated groups and precursor components having nucleophic groups, the substrate domain on the bidomain peptide is a thiol group, as present in a cysteine group attached to the amino acid sequence of the PTH. In a preferred embodiment the cysteine is attached to the N terminal site of a $PTH_{1-34}$. Also the PTH fusion peptide can be produced with a degradation site between the first and the second domains.

Degradation Sites of the PTH Fusion Peptide

An enzymatic or hydrolytic degradation site can be present between the first and the second domains of the fusion peptide. The degradation sites may be degradable by specific enzymatic degradation. This allows the release of the PTH to be controlled by cell specific processes, such as localized proteolysis. It allows PTH to be released at different rates within the matrix depending on the location of cells within the material. Preferably the degradation site is cleavable by an enzyme selected from the group consisting of plasmin and matrix metalloproteinase. By careful selection of $K_m$ and $k_{cat}$ of this enzymatic degradation site, degradation could be controlled to occur either before, or after the fibrin matrix and/or by utilizing similar or dissimilar enzymes to degrade the matrix. These degradable sites allow the engineering of more specific release of PTH from fibrin matrices. The degradable site can be cleaved by enzymes released from cells which invaded the matrix. The degradation site allows the rate of delivery to be varied at different locations within the matrix depending on cellular activity at that location and/or within the matrix. Additional benefits include the lower total drug dose within the delivery system, and spatial regulation of release which permits a greater percentage of the drug to be released at the time of greatest cellular activity. The degradation site is abbreviated "pl" in the context of the present invention.

Proteolytically degradable sites could include substrates for collagenase, plasmin, elastase, stromelysin, or plasminogen activators. Exemplary substrates are listed below. N1-N5 denotes amino acids 1-5 positions toward the amino terminus of the protein from the site were proteolysis occurs. N1'-N4' denote amino acids 1-4 positions toward the carboxy terminus of the protein from the site where proteolysis occurs.

TABLE 1

Sample substrate sequences for protease

| Protease | N5 | N4 | N3 | N2 | N1 | N1' | N2' | N3' | N4' | SEQ ID NO: |
|---|---|---|---|---|---|---|---|---|---|---|
| Plasmin[1] | | | L | I | K | M | K | P | | SEQ ID NO: 10 |
| Plasmin[1] | | | N | F | K | S | Q | L | | SEQ ID NO: 11 |
| Stromelysin[2] | Ac | G | P | L | A | L | T | A | L | SEQ ID NO: 12 |
| Stromelysin[2] | | Ac | P | F | E | L | R | A | $NH_2$ | SEQ ID NO: 13 |
| Elastase[3] | | | Z- | A | A | F | A | $NH_2$ | | SEQ ID NO: 14 |
| Collagenase[4] | | G | P | L | G | I | A | G | P | SEQ ID NO: 15 |
| t-PA[5] | | P | H | Y | G | R | S | G | G | SEQ ID NO: 16 |
| u-PA[5] | | P | G | S | G | R | S | A | S | G SEQ ID NO: 17 |

References:
[1]Takagi and Doolittle, (1975) *Biochem*. 14: 5149-5156.
[2]Smith et al., (1995). *J. Biol. Chem*. 270: 6440-6449.
[3]Besson et al., (1996) *Analytical Biochemistry* 237: 216-223.
[4]Netzel-Arnett et al., (1991) *J. Biol. Chem*.. 266: 6747-6755.
[5]Coombs et al., 1998. *J. Biol. Chem*. 273: 4323-4328.

A preferred embodiment is the sequence YKNR (SEQ ID NO: 18) between the first domain and the second domain makes the linkage plasmin degradable.

A particular preferred PTH fusion peptide is TGplPTH:

(SEQ ID NO: 19)
NQEQVSPLYKNRSVSEIQLMHNLGKHLNSMERVEWLRKKLQDVHNF

Preferred fusion proteins include:

TG-PTH$_{1-34}$: This is a modified form of PTH comprising the amino acids 1-34 of the native PTH as well as a TG (transglutaminase) substrate domain:

```
                                       (SEQ ID NO: 20)
NQEQVSPLSVSEIQLMHNLGKHLNSMERVEWLRKKLQDVHNF
```

TG-pl-PTH$_{1-34}$: This form corresponds to TG-PTH except that it additionally contains a plasmin-degradable sequence (pl) between the TG sequence and the PTH$_{1-34}$:

```
                                       (SEQ ID NO: 19)
NQEQVSPLYKNRSVSEIQLMHNLGKHLNSMERVEWLRKKLQDVHNF
```

Enzymes that could be used for proteolytic degradation are numerous. Proteolytically degradable sites could include substrates for collagenase, plasmin, elastase, stromelysin, or plasminogen activators.

In another preferred embodiment an oligo-ester domain could be inserted between the first and the second domain. This can be accomplished using an oligo-ester such as oligomers of lactic acid.

Supplemented Matrices

The PTH concentration in the matrix effective to enhance the healing of bone fractures is preferably in a range of between 0.01 to 2 mg PTH/mL matrix. When the matrix is formed from precursor solutions, like fibrinogen and thrombin or functionalized synthetic polymers, such as polyoxyalkylenes, the concentration of PTH is 0.01 to 2 mg PTH/mL of mixture of matrix precursor components. That is due to the fact that the buffer solution present in the mixture of precursor components gets incorporated in the matrix with its formation. Preferably the concentration of PTH either in the matrix or the mixture of the precursor solutions that forms the matrix is in a range of between 0.1 to 1.7 mg/mL matrix or mixture of precursor components forming the matrix, even more preferably the concentration range is in a range of between 0.3 to 1.5 mg/mL matrix or precursor components forming the matrix and most preferably in a concentration range of between 0.4 to 1.1 mg/mL matrix or mixture of precursor components forming the matrix.

If the matrix is made of a preformed material, like a collagen sponges or ceramics, the matrix is soaked in a PTH/buffer solution, leading to PTH being adsorbed and attached to the matrix by Van-der-Waals forces or ionic binding, i.e. not being covalently crosslinked to the matrix.

E. Granular Material

When the matrix is made of a soft, non-weight bearing material, like a hydrogel, a granular material may be added, preferably the granular material contains a calcium mineral. This granular material is added to support the mechanical properties of the matrix to adapt the matrix to the specific needs of the indication. This is not required if the matrix is made from a weight bearing material, like ceramics in the first place. The granular material can be any biocompatible material providing the necessary mechanical support to the composition, whereby the degree of mechanical support is dependent on the indication. Preferably the granular material is a ceramic compound and thus, in this case, the resulting final matrix is a mixture of two previously described matrix materials. Biodegradable ceramic compounds have shown favourable properties in the matrix. The ceramic compound preferably comprises a calcium mineral, like hydroxyapatite, calcium phosphate or calcium sulphate. Suitable materials include biodegradable porous mixtures of hydroxyapatite and tricalciumphosphate. Most preferred is a degradable mixture of hydroxyapatite and tricalciumphosphate. One example is a product marketed under the tradename TRICOS® (a mixture of 60% hydroxyapatite and 40% tricalciumphosphate) from Biomatlante (France). Another type of porous hydroxyapatite/tricalcium phosphate granules is CAMCERAM® from Cam Implants, Leiden (Netherlands).

It is also possible to use nonporous hydroxyapatite/tricalcium phosphate granules, pure hydroxyapatite granules (porous or nonporous), tricalcium phosphate granules (porous or nonporous), calcium sulfate granules, bone chips (either autograft or allograft) or xenograft bone chips.

II. Kits

Kits for forming the supplemented matrices described above are provided. Preferably, the kit contains at least a first and a second container. The first matrix material precursor component is provided as a first precursor solution in the first container, and the second matrix material precursor component is provided as a second precursor solution in a second container. The kit also contains PTH. The kit further contains instructions for treating a bone fracture using the components in the kit.

In one embodiment, the kit contains PTH, fibrinogen, thrombin, and a calcium source. In a preferred embodiment, the fibrinogen is provided in the first container, and thrombin in the second container. In some embodiments a calcium source is present in either the first or the second container. Optionally, the kit may contain a granular material, preferably containing a calcium mineral, and a crosslinking enzyme, such as Factor XIIIa. The granular material, if present, is provided in a separate container, for example, a syringe. Fibrinogen and thrombin can be either both or just one of them in lyophilised form. The PTH, may be present in either the fibrinogen or the thrombin solution. In a preferred embodiment the fibrinogen solution contains the PTH.

In another embodiment the kit contains PTH, a first linear or branched functionalized synthetic precursor component, like polyethylene glycol end-functionalized with nucleophilic groups, preferably thiol groups, and a further linear (only if the first precursor component is branched) or branched functionalized synthetic precursor component like polyethylene glycol end-functionalized with electrophilic groups, like conjugated unsaturated groups. The kit further contains a base solution which is separated from the other components. Optionally granules can be included in the kit.

In another embodiment, the kit contains PTH and a ceramic material, such as granules of HA, TCP or a combination thereof. The PTH may be the human sequence of PTH$_{1-84}$ or any truncated, modified and allelic version of PTH which exhibits bone formation properties. Preferred truncated versions of PTH are PTH$_{1-38}$, PTH$_{1-34}$, PTH$_{1-31}$ or PTH$_{1-25}$. Most preferred is PTH$_{1-34}$.

III. Methods of Application

The supplemented matrix may be formed in situ at the site of need in or on the body or may be pre-formed and then implanted into the desired location, i.e. at the fracture site. The supplemented matrix is used to enhance healing of bone fractures, in particular the healing of bone fractures with a risk of becoming delayed unions or non-unions and bone fractures caused by osteoporosis. Preferred indications include fractures of the wrist (distal radius fractures), long bone fractures, like fractures of the tibia, femur, fibula, radius, ulna and/or humerus further hip and vertebra fractures.

The in situ gelling/formation can occur by mixing precursor solutions, the PTH and optionally the granules and applying supplemented matrix obtained from the mixture to the fracture site. In another embodiment the supplemented matrix can be formed and or cut to shape outside the body and then applied in the preformed shape. If the matrix precursor components are reactive with each other, they should be kept separate prior to application to prevent premature polymerization. To prevent premature contact prior to administration, a kit which separates the precursor solutions from each other may be used. Upon mixing under conditions that allow polymerization, the precursor solutions form a supplemented three dimensional network. Depending on the precursor components and their concentrations, the gelling time can be tailored to the need.

The supplemented matrix should be designed such that the introduction of the matrix is possible as liquids or in a paste-like consistency which permeate and fill the bone fracture site. Solidification allows the matrix, and therefore the active agent, to be retained at the fracture site.

Cells can also be added to the supplemented matrix prior to or at the time of implantation, or even subsequent to implantation, either at or subsequent to crosslinking of the polymer to form the matrix. In a preferred embodiment the matrix has interstitial spacing designed to promote cell proliferation or in-growth.

In one embodiment fibrinogen is dissolved (which may contain additionally aprotinin to increase stability) in a buffer solution at physiological pH (in a range from pH 6.5 to 8.0, preferably from pH 7.0 to 7.5) and stored separately from a solution of thrombin in a calcium chloride buffer. The buffer solution for the fibrinogen can be a histidine buffer solution including additionally NaCl or TRIS buffer saline. Both solutions are typically stored frozen and have to be thawed prior to application.

The fibrinogen and thrombin solutions or the first and second synthetic functionalized precursor solutions are preferably mixed by a two way syringe device, in which mixing occurs by squeezing the contents of both syringes through a mixing chamber and/or needle and/or static mixer. In embodiments where both fibrinogen and thrombin or the synthetic functionalized precursor components are provided in lyophilised form, both are reconstituted prior to use. In case of fibrinogen, a tris or histidine buffer (which may additionally contain aprotinin) is added to the fibrinogen to form a fibrinogen precursor solution. Prior to use, the lyophilized thrombin is dissolved in the calcium chloride solution to form a thrombin precursor solution. Subsequently, the fibrinogen and the thrombin precursor solutions are placed in separate containers, vials or syringe bodies and mixed using a two-way connecting device, such as a two-way syringe.

Optionally, the containers, vials or syringe bodies are bipartited, thus having two chambers separated by an adjustable partition which is perpendicular to the container, vial or syringe body wall. One of the chambers contains the lyophilised precursor components, like fibrinogen or thrombin, while the other chamber contains an appropriate buffer solution. When the plunger is pressed down, the partition moves and releases the buffer into the chamber to dissolve the lyophilized component, like fibrinogen. After both components are dissolved, both bipartite syringe bodies are attached to a two way connecting device and the contents are mixed by squeezing them through the injection needle attached to the connecting device. Optionally, the connecting device contains a static mixer to improve mixing of the contents.

The granular material, if present, is wetted by injecting sterile water into the syringe. Subsequently, the above two-way syringe containing the fibrin precursor solutions and the PTH is attached to the syringe containing the wetted granular material. The content of the two-way syringe is transferred into the syringe containing the granular material. The content is subsequently injected to the site of the bone fracture and is moldable for several minutes.

While the compositions and methods have been described in terms of preferred embodiments, it will be apparent to those of skill in the art that variations may be applied to the composition, methods, kits and in the steps or in the sequence of steps of the method described herein without departing from the concept, spirit and scope of the invention.

EXAMPLES

Example 1

Bioactivity of $PTH_{1-34}$ and $TGplPTH_{1-34}$ $PTH_{1-34}$-peptide showing similar activity to the full length $PTH_{1-84}$, and proteins of this length can be synthesized by standard solid state peptide synthesis methods.

All peptides were synthesized on solid resin using an automated peptide synthesizer using standard 9-fluorenylmethyloxycarbonyl chemistry. Peptides were purified by c18 chromatography and analyzed using reverse phase chromatography via HPLC to determine purity as well as mass spectroscopy (MALDI) to identify the molecular weight of each product. Using this method, $PTH_{1-34}$ as well as, TG-pl-$PTH_{1-34}$ NQEQVPLYKNRSVSEIQLM-HNLGKHLNSMERVEWLRKKLQDVHNF (SEQ ID NO: 19) and $TGPTH_{1-34}$ NQEQVPLSVSEIQLMHNLGKHLNS-MERVEWLRKKLQDVHNF (SEQ ID NO: 20) were synthesized. $TGplPTH_{1-34}$ and $TGPTH_{1-34}$ differs from $PTH_{1-34}$ in that it additionally comprises the Factor XIIIa substrate domain which is linked to $PTH_{1-34}$ via the plasmin degradable pl-sequence YKNR (SEQ ID NO: 18) in case of $TGplPTH_{1-34}$ and directly in case of $TGPTH_{1-34}$.

To study the bioactivity of the PTH fusion peptides, a reporter gene assay was established. In this assay, a plasmid that contains luciferase reporter gene which is linked to the promoter for the parathyroid hormone receptor is transfected into cells. Then, if the cell is exposed to PTH and the PTH subsequently binds to its receptor on the cell, a signal cascade, directed through elevated cAMP levels, is initiated. Through a natural feedback regulation, this then leads to a reduction of PTH receptor levels. As the reduction is directed through the promoter, it also then leads to a decrease in production of the linked reporter gene. Using this assay, the activity of both native $PTH_{1-34}$ as well as TG-pl-PTH1-34 were studied and compared to an international standard. It was observed that both of these molecules showed a similar level of activity, as the reduction in reporter gene expression for both was the same, and this level of activity was the same as for the international standard. The results are shown in FIG. 1.

Example 2

PTH Release from a Fibrin Matrix

A fibrin matrix was made from TISSEEL® Kit (Baxter AG, CH-8604 Volketswil/ZH) fibrin precursor components. The composition is listed in Table 2. In the presence of 0.1 µg/ml of $PTH_{1-34}$ or $TGPTH_{1-34}$ was then added to the thrombin, and mixed to form a homogenous concentration. $TGPTH_{1-34}$ only has a transglutaminase sequence at the amino terminus, without a degradation site. Thus, $TGPTH_{1-34}$ can only be liberated by degradation of the fibrin matrix itself. This peptide was synthesized as described above in Example 1.

For the first release assay a fibrin matrix of 50 µl with 0.1 mg PTH or TGPTH per ml fibrin matrix was incubated at 37° C. in 10 ml buffer. Therefore, the concentration of PTH or TGPTH in the buffer in case of a total release would be 0.5 µg PTH or TGPTH/mL fibrin matrix. In order to compare the stability of PTH or TGPTH during the assay, samples of PTH or TGPTH were diluted directly in the buffer to a concentration of 0.5 µg PTH or TGPTH/mL fibrin matrix. Different buffers were tested: distilled water, phosphate buffer saline, tris-buffer saline.

Aliquots were taken at days 0, 1, 2, 4 and 6 and analysed by direct ELISA. The results showed that the PTH was not stable for more than 2 days in any of the buffers. Therefore, no conclusion could be made on the release data. The PTH stability was certainly affected by its low concentration and the buffers that were not optimal.

The release experiment was repeated by using a stabilizing buffer containing 50 mM mannitol in a 10 mM sodium acetate buffer. In addition, the buffer was exchanged every 2 days in order to prevent any degradation of peptide. The concentration of PTH or TGPTH was increased to 1 mg PTH or TGPTH/mL fibrin matrix in a 100 µl fibrin matrix and the incubation was achieved in 1 ml buffer. The concentration of PTH or TGPTH in the buffer in case of a total release would be 100 µg/mL fibrin matrix (200 times more than before). As in the first experiment, spiked samples (same amount of PTH or TGPTH dissolved in the buffer as control) were prepared to evaluate the stability of PTH or TGPTH during the experiment (100 µg/ml). Samples were collected every 2 to 4 days (with a change of buffer) during 2 weeks and analysed by direct ELISA. Spiked samples were also collected every 2 days. The results showed that under these conditions PTH and TGPTH are stable over 2 weeks.

As can be seen from FIG. 2, the major release from the fibrin matrix is achieved within 3 days. Almost 60% of PTH and 13% of TGPTH were released after day 3. These data demonstrate the retention of PTH in the fibrin matrix is highly enhanced by addition of the TG sequence.

Example 3

Sheep Tibial Defect Model

The fibrin matrix was formed starting from the TISSEEL® Kit (Baxter AG, CH-8604 Volketswil/ZH) giving 4 mL fibrin matrix. TISSEEL® is produced from human derived pooled plasma and the content of active ingredients may vary from lot to lot within predefined ranges.

Matrix:

A supplemented fibrin matrix containing granular material and PTH fusion peptide ($TGplPTH_{1-34}$) was prepared using 3 separate syringes, a two-way syringe containing fibrin precursor solution and PTH fusion peptide (syringes 1 and 2) and two one-way syringes, one containing water and the other containing granules (syringes 3 and 4). Table 2 lists the final composition used.

TABLE 2

Final Composition comprising TISSEEL ® and active component

| Ingredients | Dose per 2 mL gel |
|---|---|
| Syringe 1 (1 mL) Active Component: | |
| $PTH_{1-34}$ fusion peptide ($TGplPTH_{1-34}$) Clotting Agents | 0.4-10 mg |
| Fibrinogen (Human) Other Proteins | 66-100 mg |
| Aprotinin (Bovine) | 2046-3409 KIU |
| Human Albumin Buffer Components | 9.1-18.2 mg |
| Niacinamide | 2.7-8.2 mg |
| L-Histidine | 9.1-22.7 mg |
| Sodium Citrate | 4.4-8.8 mg |
| Polysorbate 80 | 0.6-1.7 mg |
| Water for Injection | to 1 mL |
| Syringe 2 (1 mL) Clotting Agents | |
| Thrombin (Human) Buffer Components | 2.5-6.5 I.U. |
| Calcium Chloride | 5.88 ± 0.6 mg |
| Sodium Chloride | 3.5-5.5 mg |
| Human Serum Albumin | 45-55 mg |
| Water for Injection Syringe 3 | to 1 mL |
| Water for injection Syringe 4 | 1 mL |
| Hydroxyapatite/calcium phosphate granules (TCP granules) | 1.75-2 g |

First the hydroxyapatite/calcium phosphate granules in syringe 4 were wetted by injection of the water of syringe 3. The fibrin precursor solution of syringe 1 (fibrinogen and $TGplPTH_{1-34}$ suspended in a solution with aprotinin, a serine proteinase inhibitor which helps reduce fibrolysis to retain the integrity of the fibrin matrix) was mixed with the fibrin precursor solution of syringe 2 (thrombin in a calcium chloride solution). $TGplPTH_{1-34}$ was formulated into the fibrinogen component to give a final concentration in the matrix varying from of 0.1 mg/mL to 10 mg/mL of the fibrin matrix and during the gelation process $TGplPTH_{1-34}$ became crosslinked to the matrix. Fibrin precursor solutions also contained other components of fibrin matrix, such as plasma fibronectin, Factor XIIIa, plasminogen, and human albumin. When the precursor solutions are in equal volumes, a clotting process occurs to form fibrin. The clotting process takes place over several minutes which allows for the simultaneous injection of the mixed solutions into syringe 4, which contain the wetted granules. The matrix can then be introduced at the site of need where it solidifies. Enough matrix was placed in the defect to completely fill it.

Animals:

A total of 42 Swiss Alpine, female sheep ranging between 44-83 kg (mean: 62.8 kg) and 2.25-4.75 years of age were chosen as experimental animals. Seven groups were formed with autografts as positive and fibrin matrix plus TCP granules as negative controls. The other groups consisted of the same fibrin matrix and TCP granules, but differed only in dosage of the $TGplPTH_{1-34}$. Groups were followed for 12 weeks, when animals were sacrificed at a university-owned slaughter house. All animal experiments were conducted according to the Swiss laws of animal protection and welfare and were authorized by the local Ethical Committee and Veterinary Authorities.

Surgery:

A medial approach to the tibia shaft was performed directly above the bone and extending from the distal aspect of the stifle to the hock joint, the medial fascia of the tibia was incised and the medial aspect of the tibia exposed without disturbing the periosteum. A 11 hole, 3.5 mm broad dynamic compression plate (Synthes) was contoured to the shaft with the distal end of the plate ending above the tibiotarsal joint. The plate was fixed to the bone using eleven 3.5 mm screws in a neutral position and distributing five screw holes distally and six proximally to the planned defect. The screws and plate were removed. Thereafter, the defect was marked on the bone with a scalpel blade using a gage ensuring a standardized 1 cm defect between the $5^{th}$ and $6^{th}$ screw hole. With an oscillating saw, the defect was cut under constant irrigation and preservation of soft tissues. The 1 cm segment including the circumferential periosteum was carefully removed and local bleeding out of the bone marrow or local soft tissue was stopped applying pressure with a gauze. The plate was repositioned and all screws reinserted before the matrix was filled into the bone gap as described above. Care was taken to distribute the matrix equally underneath the plate, on the lateral and as well as the transcortex.

For the positive autograft control group, autogenic bone was harvested through a local incision directly above the iliac crest. The bone marrow of the ileum was opened using multiple 3.5 mm drill holes. The cancellous bone was harvested using a curette and was immediately placed into the surgical defect at the tibia. After filling of the defects, the medial fascia was closed routinely and the skin stapled (SIGNET 35W®, Auto Sutures, Conn., USA). While the animals were still anaesthetized, radiographs were taken using medio-lateral and caudo-cranial views of the tibia. Full casts (Scotch CAST™Plus, Laboratoires 3M Santé, France) were applied involving the entire distal extremities extending up to the middle of the stifle joint at the level of the patella. The sole of the claws was left open to ensure weight bearing on the fracture site, but preventing torsional or shear forces through the immobilization of the tibial shaft through the cast.

Animals were recovered in a suspension system that prevented the animals from lying down and getting up in a hurry causing re-fracturing of the limb. The animals were kept in the suspension system for 4-5 weeks, where they could sleep, eat, defecate and urinate without interference. Thereafter, they were kept in small stalls in groups of 2-3 animals for the rest of the study period.

Cast changes were performed every 7-10 days or earlier, if animals showed problems with weight bearing, and were left in place for minimally 4 weeks but maximally 12 weeks. Follow-up radiographs through the casts were taken at 4 and 8 weeks. At the time of sacrifice (12 weeks), the radiographs were taken using a faxitron (HP Electronics) after the soft tissue, the plates and screws were removed.

Macroscopical Evaluation:

After sacrifice, the bridging of the gap was assessed macroscopically focusing on plate and fracture stability, signs of inflammation and periosteal callus formation. All bones were documented with a digital camera (Minilta, Dimage 7). Mechanical stability was tested manually only, but with caution to prevent tissue damage for future histological preparation.

Radiological Evaluation:

A semi-quantitative score system was developed to evaluate the radiographs. High scores were favourable for bone healing. The radiographs were evaluated through three independent reviewers, who were uninformed about groups and time points during the study. All radiographs were scored during one session and if scores differed, the mean scores were taken for statistical evaluation.

Histology.

Briefly, the bone sections were cut such that the entire previous gap was enclosed and the cut was made proximally and distally from the first screw hole. After fixation in 4% paraformaldehyde for 3-4 weeks, the bone blocks were washed, dehydrated in an ascending series of alcohol, defatted in xylene and finally infiltrated in acrylic resin. After infiltration was complete, polymerization was performed in Teflon forms. Sections were cut in the middle and parallel to the long axis of the bone using an Exacta band saw. Before the cut sections were mounted on acropal plastic slides, microradiographs were taken with the faxitron using a special film (Kodak PPL-2). Then sections were ground and polished to a thickness of 30-40 µm. Surface staining with toludine blue allowed differentiating between old and new bone matrix and also TCP granules.

For the thin sections (5 µm), the blocks were cut in smaller pieces containing at least one cortex and part of the periosteal and endosteal callus. Sections were mounted on positively charged, chromalaune covered glass slides, deplastified and stained with either toluidine blue or von Kossa silver staining counterstained with McNeal. In the latter, the mineralized bone matrix is stained black, whereas the uncalcified osteoid is stained blue-turquoise.

Qualitative histological evaluation was conducted by focusing on cell types, signs of inflammation and mechanisms of degradation of the matrices.

Semi-quantitative evaluation concentrated on appearance of cell types using a specially developed score system, and histomorphometrical measurements served as basis for quantitative evaluation.

For comparative purposes, different doses of $TGplPTH_{1-34}$ were tested: 0.4, 1, 2, 5 and 10 mg/ml of fibrin matrix, two control treatments were performed where no $TGplPTH_{1-34}$ was added to the fibrin-granule composite matrix (0 mg/ml) or an autograft (abbreviated "AG" in FIGS. 3 and 4) was applied (positive control). X-ray photographs were taken every four weeks and the animals were sacrificed after twelve weeks. At each time point, the X-ray photographs were analysed and the extent of bone formation was determined. Additionally, at the endpoint, the tibia was extracted for analysis via computer tomography (CT) as well as histology. Finally, as a full osteotomy was performed and then plated on one side, the defect was subject to significant stress and mechanical forces. If the material employed to treat the defect does not add significant strength, this can lead to bending of the plate and deformation of the angle. From the X-ray photographs and final samples, this is another parameter that has been measured.

The results of these experiments are shown in FIG. 3.

When the fibrin plus TCP material alone (negative control) was tested in this model, a very low healing response was observed. Of the four animals treated with this control material, none of them showed clinically healing, with one showing a moderate bone formation response and the three others showing classic signs of non-union after 12 weeks. Furthermore, within the first four weeks, all four of the animals showed significant bending of the plate and subsequent distortion of the defect.

In the next series of animals, the supplemented matrix was tested with TGplPTH$_{1-34}$ at 0.4, 1, 2, 5 or 10 mg/mL of fibrin matrix. As a first measure, these animals were observed with radiographic analysis to determine the amount of periosteal healing (callus formation). From the subsequent radiographs, it was observed that the treatment of these animals with various doses of TGplPTH$_{1-34}$ provided a dose dependent response over the range treated. Specifically, when the radiographs of these animals were examined, a much stronger periosteal healing response was observed at every time point for the doses between 0.4 and 2 mg TGplPTH$_{1-34}$/mL fibrin matrix with 0.4 and 1 mg TGplPTH$_{1-34}$/mL fibrin matrix providing statistically stronger periosteal healing when compared to those treated with the negative control material and healing that was equivalent to autograft as well at 12 weeks. Additionally, with the dose of 1 mg TGplPTH$_{1-34}$/mL fibrin matrix, it was observed that most of the animals achieved a stable union within 12 weeks (see FIG. 4). In the group treated with 1 mg TGplPTH$_{1-34}$/mL fibrin matrix, after 4 weeks, the first sign of cortical bridging and thus first signs that the healing might occur could already be observed. This response was increased significantly at the 8 week time point, where already one animal showed bridging, while the other five showed advanced bone formation. This then progressed such that after 12 weeks, 5 animals had healed showing stable, clinical unions. Furthermore, a significant improvement in stability was observed, with only one animal showing bending of the plate, which occurred within the first four weeks.

Figure 4:
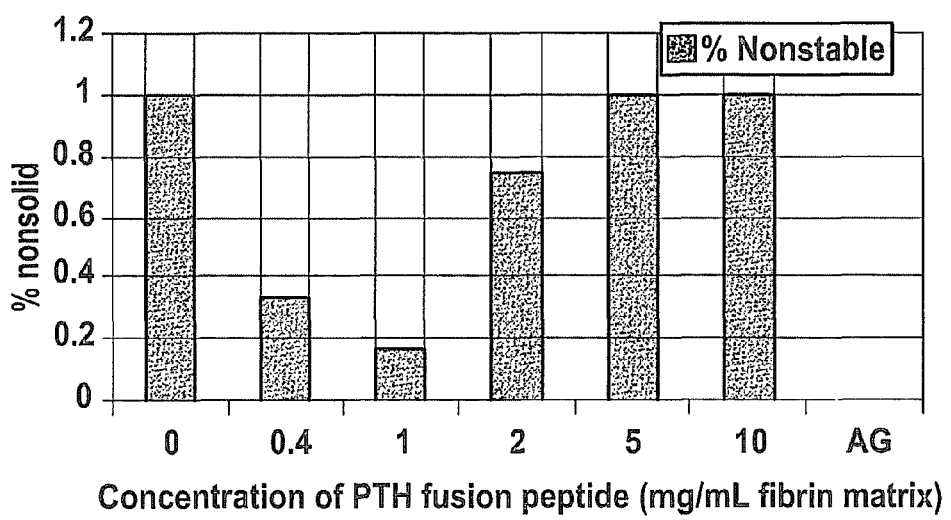
FIG. 4 shows the results of a stability test of segmental tibial defects upon treatment with the supplemented matrix, presented in percent of remaining non-stable joints.

In FIG. 4, the stability of segmental tibial defects after 12 weeks is shown. After the sheep were sacrificed at the twelfth week, the plate was removed and the stability of the original gap was lightly determined through movement/torsion of the limb. The percent of the previous fracture site that were clearly unstable was then determined. It can be seen that none the animals that were treated with autograft had unstable sites where the previous fracture had been, validating the model. Furthermore, when animals were treated with 1 mg TGplPTH$_{1-34}$/mL fibrin matrix, only one animal had an unstable fracture showing a similar strong healing response. Doses close to 1 mg TGplPTH$_{1-34}$/mL fibrin matrix also showed some stability while higher doses and the zero dose showed a much lower stability at the endpoint.

As a final measure, the rate of endosteal bone formation (formation of bone at the inner layer of long bones, i.e. inside the gap) and granule resorption was measured through histomorphometry. It was observed that with the 1 mg TGplPTH$_{1-34}$/mL fibrin matrix dose, the amount of endosteal bone formation was higher than with the other concentrations of TGplPTH$_{1-34}$, with higher doses providing lower amounts of new bone formation. Furthermore, it was observed that the rate of granule resorption was directly proportional to the rate of endosteal bone formation, with once again, the dose of 1 mg TGplPTH$_{1-34}$/mL fibrin matrix providing the best response (i.e. highest resorption rate). When the entire dose range was observed, it could be seen that higher doses provided lower rates of both endosteal bone formation and granule resorption, with the doses around 1 mg TGplPTH$_{1-34}$/mL fibrin matrix providing the best response.

The improved results in the group treated with TGplPTH$_{1-34}$ compared to the control groups demonstrated that the presence of clinically relevant doses of TGplPTH$_{1-34}$ in the supplemented matrices can lead to strong improvement in healing. The enhancement in healing, improved bone formation, as well as the improved stability in this highly mechanically stressed model are relevant characteristics to justify application of the supplemented matrix in distal radial compression fractures (see Example 6). Furthermore, in view of the results from the periosteal bone formation, endosteal bone formation and granule resorption and the overall stability, it could be seen that doses of between 0.4 mg/mL to 1.1 mg/mL TGplPTH$_{1-34}$ in fibrin matrix is the most preferred concentration range.

Example 4

Clinical Study Using a Supplemented Matrix (Fibrin Plus TGplPTH$_{1-34}$) Mixed With Hydroxyapatite/Tricalciumphosphate Granules (I-0401) to Treat Tibial Plateau Fractures This clinical study was a phase II prospective, randomized, controlled, open-label (dose-blinded), parallel-group, multi-center, dose-finding study in patients suffering from fractures of the tibial plateau that required internal fixation and grafting. This clinical study evaluated the efficacy and safety of I-0401, a supplemented matrix containing TGplPTH$_{1-34}$ and granules made of hydroxyapatite/tricalcium phosphate (HA/TCP) in a fibrin matrix at concentrations of 0.4 mg and 1 mg TGplPTH$_{1-34}$/mL fibrin matrix. This supplemented matrix was applied directly into the fracture gaps as a moldable putty that is able to form to the shape of the bone defects. This formulation was compared to treatment with autograft.

A total of 183 patients were treated at 30 centers across Europe and Australia. 59 patients were treated with 0.4 mg TGplPTH$_{1-34}$/mL fibrin matrix, 63 patients received 1.0 mg TGplPTH$_{1-34}$/mL fibrin matrix and 61 were treated with autograph. The primary endpoint was the number of patients with radiological healing based on an assessment of computed tomography (CT) scans performed by an Independent Radiology Expert Panel (IREP), at 16 weeks after treatment with I-0401. Secondary endpoints included fracture healing as assessed by the investigator, loss of reduction of the tibial plateau as assessed by the IREP using X-rays, time to radiological fracture healing, and the incidence of secondary interventions to promote fracture healing.

The primary endpoint was met, as I-0401 at 1.0 mg TGplPTH$_{1-34}$/mL fibrin matrix was shown to be non-inferior to autograft with 83.6% of the patients in the high dose I-0401 group and 84.5% of the patients in the autograft group achieving radiological fracture healing at 16 weeks after treatment. A substantial difference (p<0.03) was determined between the high and low concentrations of I-0401/mL fibrin matrix. In the low dose of I-0401 group 66.1% of the patients achieved radiological fracture healing versus 84.1% of patients in the autograph group. The results of the secondary endpoints were also supportive of the higher concentration.

At 52 weeks following treatment with I0401 or autograft, the proportion of patients with fracture healing as assessed by the investigator using radiological and clinical criteria was consistent with the assessment of radiographic fracture healing by the Independent Radiology Expert Panel (IREP), with healing seen in 96.6% of patients in the high dose I-0401 group vs. 100% of the patients in the autograph group and 96.4% of patients in the low dose I-0401 group vs. 98.2% of the patients in the autograft group. There was no clinically significant loss of reduction in any of the treatment groups compared to the post-operative assessment. Treatment with I-0401 was well tolerated with few adverse events reflecting the types of disorders expected to be observed in a population of trauma patients undergoing surgery and anesthesia.

Example 5

Clinical Study Using a Supplemented Matrix (Fibrin Plus TGplPTH$_{1-34}$) (I-040202) to treat Tibia Shaft Fractures This was a Phase II, prospective, randomized, controlled, open-label (dose-blinded), parallel-group, multi-center clinical study of the efficacy and safety of TGplPTH$_{1-34}$ in a matrix made of fibrin (I-040202) in patients with acute, open tibial shaft fractures. The supplemented matrix was applied directly to the fracture site in the form of a paste. A total of 200 patients were randomized and treated in 31 centers across Europe.

The study consisted of four study groups: one control group using standard of care (SoC) which included intramedullary nailing and soft tissue management, and three treatment groups using 4 mL of I-040202 containing TGplPTH$_{1-34}$ at concentrations of 0.133, 0.4 and 1.0 mg/mL fibrin matrix respectively (different concentrations of TGplPTH$_{1-34}$), as an adjunct to SoC. Patients followed up clinically and radiologically on a monthly basis until 6 months post-surgery, and thereafter at 9 and 12 months post-surgery.

The primary endpoint was the proportion of patients who had fracture healing at 6 months as assessed by the investigator using radiographic and clinical parameters. Three doses of I-040202 in combination with SoC were compared against SoC alone. The study met its primary endpoint, with a statistically higher healing rate in patients treated with I-040202 than those receiving standard of care alone.

The results related to the primary endpoint of the trial were as follows:

TABLE 3

Investigator's Healing Assessment,
Intent-to-Treat population - Primary endpoint

| Treatment | % healed at 6 months (Clinician's assessment) | |
|---|---|---|
| | % (n of N) | 90% CI for Proportion |
| SoC alone | 64.6% (31 of 48) | 52.8% to 75.2% |
| 0.133 mg TGplPTH$_{1-34}$/ml fibrin matrix + SoC | 75.6% (34 of 45) | 64.1% to 85.0% |
| 0.4 mg TGplPTH$_{1-34}$/ml fibrin matrix + SoC | 80.4%* (37 of 46) | 69.7% to 88.8% |
| 1.0 mg TGplPTH$_{1-34}$/ml fibrin matrix + SoC | 69.2% (27 of 39) | 56.4% to 80.3% |

*Statistically better than standard of care alone (p = 0.084). Type 1 error set at 0.1.

Example 6

Study Using a Supplemented Matrix (PEG Hydrogel Plus cPTH$_{1-34}$)

The first precursor was a branched PEG with four arms and a molecular weight of 15 kDa, functionalyzed with 4 acrylic groups at the end of each arm (PEG15ACR4). The first precursor component consisted of a pentaerythritol to which 4 PEG chains were attached by ether bonds. The second precursor was a linear PEG with a molecular weight of 3.4 kDa and functionalized with thiol groups at each end of the chain (PEG3.4SH2). When activated by alkaline pH, the thiol groups on the linear PEG3.4SH2 reacted with the acrylate groups of the PEG15ACR4 through a Michael-type addition reaction and a new covalent link was formed.

The two precursor components were dissolved separately into a buffer and the two solutions obtained were mixed to generate the matrix within a few minutes. The amounts of each precursor component were calculated to be at equinormal concentrations.

The ester bonds linking the acrylic functional groups to the PEG chains of the 4 arm polymer are susceptible to hydrolysis, which allows the degradation of the hydrogel in vitro and in vivo.

cPTH$_{1-34}$

The bioactive component contained a PTH$_{1-34}$ variant, modified with the addition of a cysteine residue, at the N-terminus of the peptide (cPTH$_{1-34}$). The thiol group of the cysteine reacted in the Michael-type addition with the PEG functionalized with acrylic groups. This results in the covalent linkage of the cPTH$_{1-34}$ into the hydrogel matrix. cPTH$_{1-34}$ was used at a concentration of 0.4 mg cPTH$_{1-34}$/mL PEG matrix.

Sequence of the PTH$_{1-34}$ variant

| Cys-PTH 1-34 (cPTH) | Cys-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe, i.e. CSVSEIQLMHNLGKHLNSMERVEWLRKKLQDVHNF (SEQ ID NO: 21) |
|---|---|

Test Item Preparation

Synthetic Hydrogel Containing 0.4 mg cPTH$_{1-34}$/mL PEG

PEG precursors and cPTH$_{1-34}$ were weighed directly in 5 mL syringes and dissolved in the reconstitution buffers just before the surgery. TRIS/HCl buffer (100 mM, pH 8.0) with or without cPTH$_{1-34}$ was used as reconstitution and gelation buffer.

cPTH$_{1-34}$ was used as concentrated stock solution in water to prepare the reconstitution/gelation buffer for PEG15ACR4 at the bioactive dose required. Concentrations of the stock solutions were calculated taking into account the protein content and purity of the commercial products.

PEG3.4SH2 was reconstituted by connecting the syringe in which it was contained to a second syringe filled with the gelation buffer and by mixing back and forth by pushing the plungers. PEG15ACR4 was reconstituted by connecting the syringe in which it was contained to a second syringe filled with gelation buffer, in which the dose of the bioactive had been incorporated, and by mixing back and forth by pushing the plungers. Each resulting solution was filtered by 0.22 µm filters and collected into a new sterile syringe. The resulting two sterile syringes containing sterile solutions of PEG precursors were connected to each other by a sterile connector and the solutions vigorously mixed back and forth ~10 times, in order to produce an even mixture. The mixture was transferred into a sterile Optimed Cemento® cement gun used without the trocaire. 4 mL of this mixture was applied. A stopwatch was used to check the time elapsed from the start of the mixing until application. The large neck of the cement gun Optimed Cemento RE (3.3 mm against 2.4 mm of a BD plastic syringe), allowed an easy delivery of the thickened solution and the extension of the surgeon's working time. In all cases 4 mL of product were delivered into the defect about four to six minutes after mixing the hydrogel precursors.

The surgical procedure is the same as described in Example 3. The supplemented matrix was filled into the segmental defect site, and distributed equally underneath the plate to fill the defect completely. While the animals were still anaesthetized, radiographs were taken using medio-lateral and caudo-cranial views of the tibia. Full casts (Scotch Cast™Plus, 7.6 cm, Laboratoires 3M Santé, France) were applied involving the entire distal extremity, extending up to the middle of the stifle joint at the level of the patella. The sole of the hoof was left exposed to ensure weight bearing on the fracture site, but preventing torsional or shear forces through the immobilization of the tibia shaft through the cast.

Cast changes were performed every seven to ten days or earlier if the animals showed problems with weight bearing. They were left in place for a minimum of eight up to a maximum of twelve weeks. Radiographs were taken at four, eight and twelve weeks; at the time of the sacrifice, the tibias were extracted for analysis by radiography and µCT.

Results

The scoring was performed in one session by two independent reviewers who were blinded to the treatment groups and time-points in the study. The two-dimensional lateral and antero-posterior images (along the z-axis, xz and yz) were used for the evaluation. The scorers assigned a score from 1 (one) to 4 (four) depending on the number of bridged cortices. The bone was considered bridged when 2 out of 4 cortices were bridged No signs of toxicity or deaths related to the administration of the treatments were observed during the study.

In the evaluation of the healing at twelve weeks, autograft showed bridging in 3 out of 4 of the animals (75%). The empty group showed bridging in 1 out of 6 animals (16.6%). The animals treated with the PEG-cPTH 0.4 mg/mL PEG matrix showed bridging in 5 out of 6 animals (83.3%) (Table 4).

TABLE 4

Radiograpical evaluation of the bone bridging after 12 weeks

| Treatment | Bridged defects | Total of animals | % bridged | % normalized to autograft |
|---|---|---|---|---|
| Autograft | 3 | 4 | 75 | 100 |
| Empty | 1 | 6 | 16.6 | 22.2 |
| PEG 0.4 mg cPTH$_{1-34}$/ml | 5 | 6 | 83.3 | 111 |

The residency time of the hydrogel in the bone defect is below 12 weeks as the hydrogel was resorbed at this time point (~10% of the area analyzed on the thin slices still showed residual material in 4 out of 6 groups).

We claim:

1. A method of repairing a bone fracture, comprising administering to the site of the bone fracture, a formulation capable of forming a supplemented matrix under physiological conditions,
    wherein the bone fracture is a discontinuity in the bone structure which results in two or more distinct bone segments of the fractured bone,
and forming a supplemented matrix at the site,
wherein the supplemented matrix comprises
    (i) PTH or a PTH fusion peptide
    (ii) a matrix material comprising fibrin,
    wherein the PTH or PTH fusion peptide is present in an effective amount to rejoin and realign the segments of the fractured bone.

2. The method of claim 1, wherein the supplemented matrix further comprises a granular material comprising a calcium mineral.

3. The method according to claim 1, wherein the bone fracture is a fracture of the distal radius, tibia, femur, fibula, radius, ulna, humerus, hip, or vertebra.

4. The method of claim 1, wherein the fracture is a long bone fracture.

5. The method of claim 1, wherein the PTH or PTH fusion peptide is present in a concentration range of between 0.01 and 2 mg/mL matrix.

6. The method of claim 1, wherein the supplemented matrix is administered by injecting a formulation capable of forming a fibrin matrix into the site of the bone fracture, wherein the formulation comprises
(i) a peptide selected from the group consisting of PTH and a PTH fusion peptide;
(ii) a fibrinogen precursor component; and
(iii) a thrombin precursor component,
wherein the PTH or PTH fusion peptide is present in a concentration range of between 0.01 to 2 mg/mL fibrin matrix or precursor components forming the matrix.

7. The method of claim 1, wherein the site is in a human.

8. The method of claim 6 wherein the fibrinogen precursor component or the thrombin precursor component further comprises a calcium ion source.

9. The method of claim 6, wherein the formulation further comprises a granular material comprising a calcium mineral.

10. The method of claim 1, wherein the PTH fusion peptide comprises at least two domains wherein the first domain comprises PTH and the second domain comprises a crosslinkable substrate domain.

11. The method of claim 1, wherein the PTH is selected from the group consisting of $PTH_{1-84}$, $PTH_{1-38}$, $PTH_{1-34}$, $PTH_{1-31}$ and $PTH_{1-25}$.

12. The method of claim 11, wherein the PTH is $PTH_{1-34}$.

13. The method of claim 10, wherein the second domain comprises a transglutaminase substrate domain.

14. The method of claim 13, wherein the transglutaminase domain comprises a Factor XIIIa substrate domain.

15. The method of claim 10, wherein PTH fusion peptide further comprises a degradation site between the first and the second domains.

16. The method of claim 2, wherein the granular material is a mixture of tricalcium phosphate and hydroxyapatite.

17. The method of claim 3, wherein the site is the tibia.

18. The method of claim 2, wherein the granular material is selected from the group consisting of hydroxyapatite, calcium phosphate and calcium sulphate and combinations thereof.

* * * * *